United States Patent [19]

Franzmann

[11] Patent Number: 4,968,698

[45] Date of Patent: Nov. 6, 1990

[54] NITROGEN CONTAINING HETEROCYCLIC COMPOUNDS

[75] Inventor: Karl W. Franzmann, Kent, England

[73] Assignee: Burroughs Wellcome Co., Research Triangle Park, N.C.

[21] Appl. No.: 279,427

[22] Filed: Dec. 2, 1988

Related U.S. Application Data

[60] Division of Ser. No. 61,599, Jun. 18, 1987, abandoned, which is a continuation of Ser. No. 758,097, Jul. 23, 1985, abandoned.

[30] Foreign Application Priority Data

Aug. 1, 1984 [GB] United Kingdom ............... 8419658

[51] Int. Cl.$^5$ ................... A61K 31/47; C07D 405/06; C07D 409/06
[52] U.S. Cl. .................................. 514/307; 514/309; 546/141; 546/145; 546/146; 546/149; 546/150
[58] Field of Search ............... 514/207, 309; 546/150, 546/149, 145–146, 141

[56] References Cited

U.S. PATENT DOCUMENTS

| | | | |
|---|---|---|---|
| 3,067,203 | 12/1962 | Besendorf et al. | 546/150 |
| 3,146,266 | 8/1964 | Besendorf et al. | 546/150 |
| 3,823,148 | 9/1974 | Jansen et al. | 546/150 |

FOREIGN PATENT DOCUMENTS

| | | |
|---|---|---|
| 113277 | 6/1941 | Australia . |
| 259086 | 5/1963 | Australia . |
| 862052 | 3/1961 | United Kingdom . |
| 1181959 | 2/1970 | United Kingdom . |

OTHER PUBLICATIONS

Harmon et al., "J.O.C.", vol. 35, No. 3, 1970, pp. 825–827.
Kametani et al., "Chemical Abstracts", vol. 70, 1969, col. 77754b.
Markwardt et al., "Chemical Abstracts", vol. 72, 1970, col. 29987z.
Markwardt et al., "Chemical Abstracts", vol. 72, 1970, col. 100540f.
Dietz et al., "Chemical Abstracts", vol. 76, 1972, col. 14283a.
Comer et al., "Chemical Abstracts", vol. 79, 1973, col. 126294y.
Tetrahedron Letters No. 28, pp. 2433–2436, 1976, Pergamon Press, printed in Great Britain.
Child and Pyman, pp. 36–49.
Chem. Ber. 1961, 94, 199–201.
Organic Reactions, The Ritter Reaction, Chap. 3, L. Krimen et al., pp. 213–259.
Journal of the American Chemical Society, 94:8, Apr. 19, 1972, pp. 2874–2875.
"Chemical Abstracts", 29–Organometallics; vol. 89, 1978, p. 583.
"Chemical Abstracts", vol. 62, 1965, 37–Heterocyclic Compounds.
Organic Reactions, 1951, VI, 74, pp. 98–99.
J. Chem. Soc. (C), 1969, pp. 94–100.

*Primary Examiner*—Glennon H. Hollrah
*Assistant Examiner*—James H. Turnipseed
*Attorney, Agent, or Firm*—Donald Brown

[57] ABSTRACT

Compounds of the formula (III):

$$
\begin{array}{c}
\text{(III)}
\end{array}
$$

(structure with substituents $R^1$, $R^2$, $R^3$, $R^4$, $R^{5a}$, $R^{5b}$, $R^{6a}$, $R^{6b}$, $R^8$, $CR^7R^9$, $(R^0)_m$)

or salts or acyl derivatives thereof, for use as antifungal and antiprotozoal agents are disclosed. Compositions containing the compounds are also disclosed as are method for the preparation of the compounds and intermediates in their preparation.

5 Claims, No Drawings

NITROGEN CONTAINING HETEROCYCLIC COMPOUNDS

This patent application is a divisional of co-pending application U.S. Ser. No. 07/061,599 filed on Jun. 18, 1987, now abandoned, which is a continuation of U.S. Ser. No. 06/758,097 filed Jul. 23, 1985, now abandoned.

The present invention relates to a group of compounds which are useful in the treatment of certain microbial and fungal infections, to compositions containing the compounds and to intermediates in the preparation of the compounds.

British Patent No. 1181959 discloses that compounds of the formula (I):

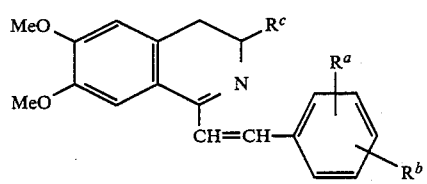

wherein $R^a$ and $R^b$ are hydrogen or chlorine and $R^c$ is hydrogen or methyl are effective in the prophylaxis of thrombosis.

U.S. Pat. No. 3823148 discloses inter alia compounds of the formula (II):

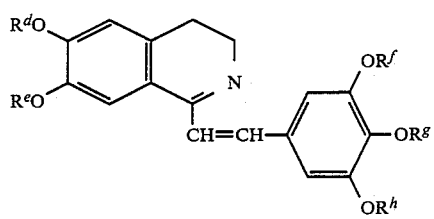

wherein $R^d$ and $R^e$ are hydrogen, lower alkyl or benzyl or together form a methylene bridge and $R^f$, $R^g$ and $R^h$ are each hydrogen or lower alkyl, as having hypotensive and CNS activity. Specifically disclosed is the compound of the formula (II) wherein $R^d$-$R^h$ are each methyl.

It has now been discovered that a group of vinylisoquinolines including, inter alia compounds of the formula (I) and (II), has activity against protozoa, particularly those of the genus Trichomonas, for example Trichomonas vaginalis, an organism responsible for causing irritation of the vaginal mucosa and consequent abnormal vaginal discharge.

Accordingly the present invention provides a compound for use as an antiprotozoal agent, the said compound being a compound of the formula (III):

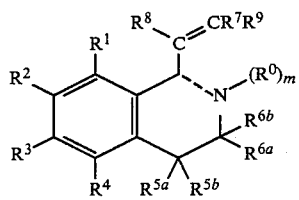

or a salt or acyl derivative thereof, wherein the dotted line represents either a single or a double bond;

m is 0 when the dotted line represents a double bond, or m is 1 when the dotted line represents a single bond;

$R^o$ is hydrogen or a group $CH_2R^{10}$;

$R^1$ is hydrogen, or a substituent chosen from fluorine, chlorine, methoxy, methyl, trifluoromethyl or methylthio;

$R^2$, $R^3$ and $R^4$ are the same or different and each is hydrogen or a substituent group of the formula $R^{10}$-A-wherein $R^{10}$ is hydrogen or $C_{1-16}$ hydrocarbyl optionally substituted by halogen, fluorosulphonyl, cyano, hydroxy, thio, nitro, $C_{1-3}$ alkoxy or $C_{1-3}$ alkylthio wherein the alkoxy and alkylthio groups are optionally further substituted by halogen, hydroxy, thio, $C_{1-2}$ alkoxy or $C_{1-2}$ alkylthio, and A is oxygen, sulphur or methylene; or any two adjacent substituents $R^1$-$R^4$ together form a methylenedioxy or ethylenedioxy group;

$R^{5a}$ is hydrogen or $C_{1-12}$ hydrocarbyl and $R^{5b}$ is hydrogen or $R^{5a}$ and $R^{5b}$ are each $C_{1-4}$ alkyl or $R^{5a}$ and $R^{5b}$ together with the carbon atom to which they are attached, form a $C_{3-8}$ spirocycloalkyl ring;

$R^{6a}$ and $R^{6b}$ are the same or different and each is hydrogen or $C_{1-12}$ hydrocarbyl or, together with the carbon atom to which they are attached, form a $C_{3-8}$ spirocycloalkyl ring; or $R^{5a}$ and $R^{6a}$ together with the carbon atoms to which they are attached form a five or six membered carbocyclic ring optionally containing up to two double bonds;

$R^7$ is hydrogen or fluorine;

$R^8$ is hydrogen, halogen, cyano, nitro or $C_{1-2}$ alkyl optionally substituted by one or more halogen atoms;

$R^9$ is a group $-(CH=CH)_n R^{11}$ wherein n is 0–2 and $R^{11}$ is hydrogen, $C_{1-8}$ alkyl, $C_{2-8}$ alkenyl, $C_{2-8}$ alkynyl or a monocyclic, bicyclic, tricyclic or tetracyclic ring system containing between three and sixteen ring members, optionally substituted by hydroxy, thio, halogen, fluorosulphonyl, nitro, cyano, $C_{1-12}$ hydrocarbyl, $C_{1-12}$ hydrocarbyloxy, $C_{1-12}$ hydrocarbylthio wherein the said hydrocarbyl, hydrocarbyloxy and hydrocarbylthio groups are each optionally further substituted by halogen, hydroxy, thio, $C_{1-2}$ alkylthio or $C_{1-2}$ alkoxy groups; the groups $R^8$ and $R^9$ optionally being linked through a $C_{1-4}$ alkylene bridge.

When m=1, suitably $R^o$ is hydrogen, $C_{1-4}$ alkyl or optionally substituted benzyl and preferably $R^o$ is hydrogen, methyl, ethyl or benzyl.

Suitably $R^1$ is hydrogen, fluorine or methoxy and preferably it is hydrogen or methoxy.

$R^2$, $R^3$ and $R^4$ preferably are chosen from hydrogen, $C_{1-10}$ alkyl, $C_{1-10}$ alkoxy, benzyloxy, phenyloxy, $C_{3-7}$ cycloalkyloxy, $C_{4-10}$ cycloalkylalkyloxy and $C_{3-6}$ alkenyloxy, each optionally substituted as hereinbefore defined.

$R^{5a}$ suitably is hydrogen, $C_{1-4}$ alkyl, phenyl or benzyl and preferably is hydrogen or methyl. $R^{5b}$ preferably is hydrogen or methyl.

$R^{6a}$ and $R^{6b}$ suitably are hydrogen or $C_{1-4}$ alkyl; $R^7$ preferably is hydrogen and $R^8$ preferably is hydrogen, fluorine, chlorine, bromine or methyl When $R^{11}$ is a monocyclic, bicyclic, tricyclic or tetracyclic ring system, it is either saturated, partially saturated or unsaturated. The ring system is either carbocyclic or heterocyclic and, when it is heterocyclic, it may contain up to three heteroatomic ring members, suitably chosen from oxygen, sulphur or nitrogen. Preferably, when there are more than one heteroatomic ring members, only one of these is nitrogen. Preferred ring systems are naphthyl, phenyl, anthryl, phenanthryl, $C_{3-8}$ cycloalkyl, $C_{5-8}$ cycloalkenyl, thienyl, furanyl, indolyl pyridyl, quinolyl, isoquinolyl or reduced or partially reduced derivatives thereof.

Preferably, when $R^{11}$ is a monocyclic, bicyclic, tricyclic or tetracyclic ring system, n is 0 or 1.

Other protozoa against which compounds of the present invention are active include Coccidia, Leishmania, Plasmodium, Trypanosoma, intestinal flagellates such as *Giardia lamblia*, amoeba such as *Entamoeba histolytica* and the protozoal organism responsible for the cattle disease Babesia.

Many of the compounds of the present invention have also been found to possess broad spectrum antifungal activity. Fungi against which they are active include those pathogenic in man, animals and plants, for example: *Candida albicans, Candida tropicalis, Cryptococcus neoformans, Saccharomyces cerevisiae, Aspergillus fumigatus, Aspergillus niger, Microsporum canis, Microsporum gypseum, Trichophyton equinum, Trichophyton mentagrophytes, Trichophyton rubrum, Epidermophyton floccosum,* and *Exophiala werneckii*, Fusarium species such as *Fusarium solani, Sporothrix schenckii,* Penicillium species such as *P. rubrum,* Alternaria species, *Ceratocystis pilifera, Chrysosporium pruinosum,* Helminthsporium species and *Paecilomyces variotti*.

Accordingly, the present invention also provides a compound for use against fungal infections, the said compound being a compound of the formula (IIIA);

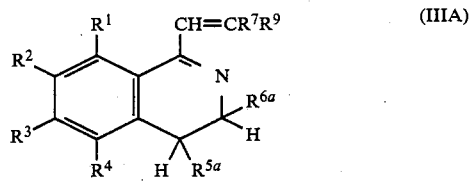

(IIIA)

or a salt or acyl derivative thereof, wherein $R^1$-$R^7$ and $R^9$ are as hereinbefore defined, except that $R^{11}$ is a group $R^{13}$ wherein $R^{13}$ is hydrogen, $C_{1-8}$ alkyl, $C_{2-8}$ alkenyl, $C_{2-8}$ alkynyl or a monocyclic or bicyclic ring system containing three to ten ring members, optionally substituted by hydroxy, thio, halogen, fluorosulphonyl, nitro, cyano, $C_{1-12}$ hydrocarbyl, $C_{1-12}$ hydrocarbyloxy, $C_{1-12}$ hydrocarbylthio wherein the said hydrocarbyl, hydrocarbyloxy and hydrocarbylthio group are each optionally further substituted by halogen, hydroxy, thio, $C_{1-2}$ alkylthio or $C_{1-2}$ alkoxy.

Preferred substituents $R^1$-$R^7$ and $R^9$ are those defined above in respect of compound (III).

The above mentioned compounds have been found to be particularly useful in the treatment of infections caused by the yeast-like fungus *Candida albicans* and closely related organisms. Such infections are generically referred to as Candidiasis or Moniliasis and include, for example, vaginal candidiasis.

In another aspect, therefore, the present invention provides a compound of the formula (IIIA), or salts or acyl derivatives thereof, for use against Candidal infections in mammals. In particular, there is provided a compound of the formula (IIIA) for use against Candidal infections in humans.

The invention further provides a compound of the formula (IIIA) for use in the treatment or prevention of fungal infections in plants and plant products, for example timber.

Many of the compounds of the present invention are novel and thus in a further aspect, the present invention provides a class of novel compounds, the said novel compounds having the general formula (III) as hereinbefore defined but with the proviso that (i) when $R^2$ and $R^3$ are the same or different and each is hydroxy, methoxy or ethoxy; or when $R^2$ and $R^3$ together form a methylenedioxy or ethylenedioxy group; or when $R^2$ is benzyloxy and $R^3$ is methoxy, $R^1$ must be a group $R^{12}$ wherein $R^{12}$ is fluorine, chlorine, methyl, trifluoromethyl or methylthio and/or $R^4$ must be a substituent as hereinbefore defined, or (ii) when $R^3$ and $R^4$ are each methoxy and $R^9$ is a phenyl group bearing a 2-chloro and a 5-nitro substituent, the phenyl group is additionally substituted by a substituent as hereinbefore defined and/or at least one of $R^1$, $R^2$ and $R^{5a}$-$R^8$ is a substituent as hereinbefore defined, or (iii) when $R^1$-$R^4$ are each hydrogen and $R^9$ is hydrogen, methyl or unsubstituted phenyl, $R^{5a}$ and/or $R^{5b}$ are substituents as hereinbefore defined, or (iv) when $R^1$-$R^4$ are each hydrogen and $R^9$ is a phenyl group bearing bromo, chloro, hydroxy, methyl, methoxy or nitro substituents, the phenyl ring is trisubstituted by substituents as hereinbefore defined, or (v) when $R^9$ is a phenyl group substituted at the 3-, 4- and 5- positions with hydroxy or $C_{1-6}$ alkoxy and $R^2$ and $R^3$ are each hydroxy, $C_{1-4}$ alkoxy or benzyloxy, at least one of $R^1$, $R^4$, $R^7$ and $R^8$ is a substituent as hereinbefore defined.

The terms substituted and substituent used above and hereinafter are used in their conventional sense, is to denote the attachment to a particular atom or molecule of an atom or group other than hydrogen.

Preferred novel compounds of the present invention include those wherein $R^3$ is a group $R^{14}$-A-, and $R^1$, $R^2$, $R^4$-$R^9$ are as hereinbefore defined, $R^{14}$-A-being $C_{3-16}$ hydrocarbyl optionally substituted as defined hereinabove in respect of $R^{10}$. More preferred novel compounds of the present invention are those wherein $R^1$, $R^2$ and $R^4$-$R^9$ are preferred substituents as hereinbefore defined and $R^{14}$-A-is $C_{3-6}$ alkoxy, benzyloxy, phenyloxy, $C_{3-7}$ cycloalkyloxy, $C_{4-8}$ cycloalkylalkyloxy and $C_{3-6}$ alkenyloxy, each optionally substituted as hereinbefore defined. Particularly preferred compounds are those wherein $R^{14}$-A-is chosen from the preferred substituents described above and $R^2$ and $R^4$ are each hydrogen, $C_{1-4}$ alkoxy or $C_{1-4}$ alkyl. A most preferred group of compounds is that wherein $R^2$ and $R^4$ are hydrogen.

A preferred group of novel compounds of the present invention is that of the formula (IV):

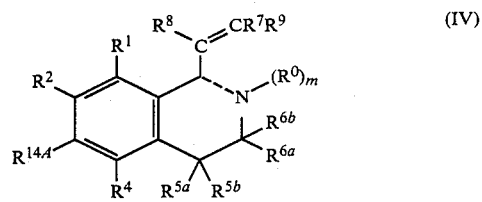

(IV)

or salts or acyl derivatives thereof, wherein the dotted line represents either a single or a double bond and m, $R^o$, $R^1$, $R^2$, $R^4$, $R^9$ and $R^{14}$-A-are as hereinbefore defined, except that when the group $C(R^8)=CR^7 R^9$ is 3,4,5-trihydroxystyryl or a mono-, di- or tri-ether thereof, $R^2$ is other than hydroxy, $C_{1-4}$ alkoxy or benzyloxy and/or one or both of $R^1$ and $R^4$ are substituents as hereinbefore defined.

A further preferred group of novel compounds of the present invention is that of the formula (V):

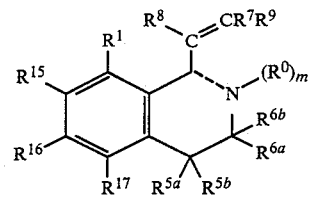

(V)

or salts or acyl derivatives thereof,
wherein
m, $R^o$, $R^1$ and $R^5$–$R^9$ are as hereinbefore defined;
$R^{15}$ is hydrogen or a substituent group $R^{18}$-A-wherein A is as hereinbefore defined and $R^{18}$ is hydrogen, $C_{3-6}$ alkyl, $C_{3-7}$ cycloalkyl, $C_{4-8}$ cycloalkylalkyl, or phenyl each optionally substituted by one or more halogen, cyano, nitro, hydroxy, thio, $C_{1-2}$ alkoxy or $C_{1-2}$ alkylthio;
$R^{16}$ is a group $R^{19}$-A-wherein A is as hereinbefore defined and $R^{19}$ is hydrogen, $C_{1-2}$ alkyl, ethenyl or ethynyl; $R^{17}$ is hydrogen or a group $R^{14}$-A-as hereinbefore defined.

Preferred substituents $R^1$ and $R^5$–$R^9$ are those defined in respect of formula (III). Preferred groups of the formulae $R^{18}$-A-, $R^{19}$-A-and $R^{14}$-A-are those in which A is oxygen or methylene. A most preferred group of the formula $R^{19}$-A-is that wherein A is oxygen.

Another preferred group of novel compounds provided by the present invention is that of the formula (VI):

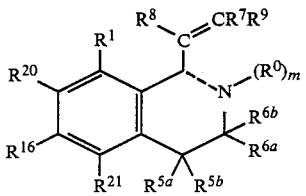

(VI)

or salts or acyl derivatives thereof, wherein m, $R^o$, $R^1$, $R^{16}$ and $R^5$–$R^9$ are as hereinabove defined and $R^{20}$ and $R^{21}$ are the same or different and each is a group $R^{10}$A- as hereinbefore defined.

A still further preferred group of novel compounds are those of the formula (VII):

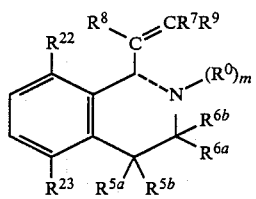

(VII)

or salts or acyl derivatives thereof, wherein $R^{22}$ is methoxy or a group $R^{12}$ and $R^{23}$ is a group $R^{10}$A-and m[$R^o$] $R^{10}$A, $R^{12}$ and $R^5$–$R^8$ are as hereinbefore defined.

One preferred group of compounds of the formula (IV) is that of the formula (VIII):

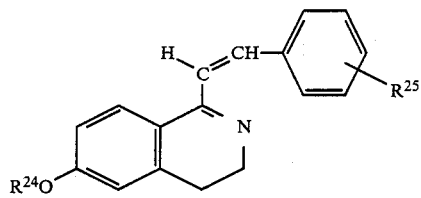

(VIII)

or a salt or acyl derivative thereof, wherein $R^{24}$ is $C_{3-10}$ alkyl, benzyl, phenyl, $C_{3-7}$ cycloalkyl, $C_{4-8}$ cycloalkylalkyl and $C_{3-10}$ alkenyl each optionally substituted by halogen, cyano, hydroxy, thio, nitro, $C_{1-3}$ alkoxy or $C_{1-3}$ alkylthio wherein the alkoxy and alkylthio groups are optionally further substituted by halogen, hydroxy, thio, $C_{1-2}$ alkoxy or $C_{1-2}$ alkylthio and $R^{25}$ is hydrogen or up to five substituents chosen from hydroxy, $C_{1-12}$ hydrocarbyloxy, thio, $C_{1-12}$ hydrocarbylthio, halogen, nitro, cyano or $C_{1-12}$ hydrocarbyl, the said hydrocarbyl, hydrocarbylthio or hydrocarbyloxy groups being each optionally further substituted by halogen, hydroxy, thio, $C_{1-2}$ alkylthio or $C_{1-2}$ alkoxy groups. Most preferably, $R^{25}$ is phenyl or up to two substituents chosen from halogen, nitro, cyano, hydroxy, $C_{1-2}$ alkoxy and $C_{1-4}$ alkyl.

Another preferred group of compounds of the formula (IV) is that of the formula (IX):

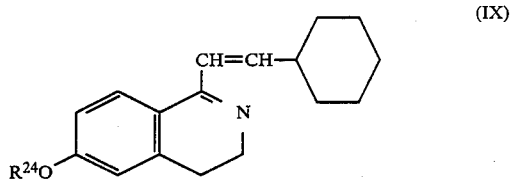

(IX)

or a salt or acyl derivative thereof, wherein $R^{24}$ is as hereinbefore defined.

Still another preferred group of compounds of the formula (IV) is that of the formula (X):

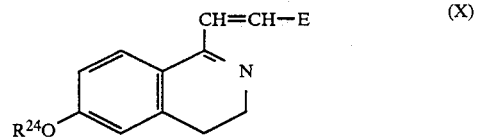

(X)

or a salt or acyl derivative thereof, wherein E represents a five or six membered ring containing one heteroatomic ring member chosen from oxygen, sulphur and nitrogen, the ring being optionally substituted by one or two groups chosen from hydroxy, $C_{1-2}$ alkoxy, halogen, $C_{1-2}$ alkyl, nitro or cyano. Preferred heterocyclic rings are pyridyl, thienyl and furyl.

An additional preferred group of compounds of the formula (IV) is that of the formula (XI):

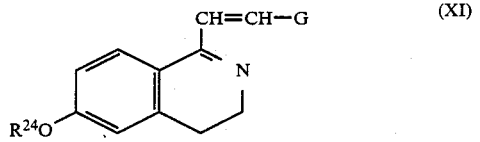

(XI)

or salts or acyl derivatives thereof, wherein G is an optionally substituted bicyclic or tricyclic group as hereinbefore defined. Preferred bicyclic groups are naphthyl, anthryl, phenanthryl, indolyl, quinolyl and isoquinolyl or reduced or partially reduced derivatives thereof.

Yet another preferred group of compounds of the formula (IV) is that of the general formula (XII):

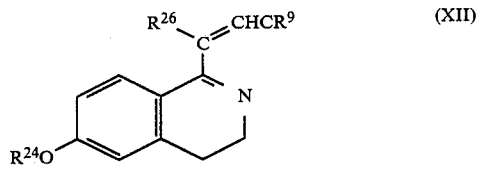

or a salt or acyl derivative thereof, wherein $R^{26}$ is chosen from fluorine, chlorine, bromine and methyl.

Preferred novel compounds of the present invention include:

1. (E)-6-Butyloxy-1-(2-cyclohexylvinyl)-3,4-dihydroisoquinoline
2. 6-Benzyloxy-1-[2-cyclohexylvinyl]-3,4-dihydroisoquinoline
3. 6-Butyloxy-3,4-dihydro-1-styrylisoquinoline
4. 1-(2-Chlorostyryl)-3,4-dihydro-6-propyloxyisoquinoline
5. (E)-1-(2-Cyclohexylvinyl)-3,4-dihydro-6-(2-methylpropyloxy)isoquinoline
6. (E)-1-(2-Cyclohexylvinyl)-3,4-dihydro-6-propyloxyisoquinoline
7. (E)-1-(Cyclohexylvinyl)-6-hexyloxy-3,4-dihydroisoquinoline
8. (E)-6-(4-Chlorobenzyloxy)-1-(2-cyclohexylvinyl)-3,4-dihydroisoquinoline
9. (E)-6-Benzyloxy-1-[2-(cyclohex-3-enyl)vinyl]-3,4-dihydroisoquinoline
10. 6-Butyloxy-3,4-dihydro-1-(2,5-dimethoxystyryl)isoquinoline
11. 6-Butyloxy-3,4-dihydro-1-(3,4,5-trimethoxystyryl)isoquinoline
12. 6-Butyloxy-1-(2-chlorostyryl)-3,4-dihydroisoquinoline
13. 6-Butyloxy-3,4-dihydro-1-(4-cyanostyryl)isoquinoline
14. 6-Butyloxy-3,4-dihydro-1-(2,4-dimethoxystyryl)isoquinoline
15. 6-Butyloxy-1-(4-t-butylstyryl)-3,4-dihydroisoquinoline
16. 6-Butyloxy-3,4-dihydro-1-(4-isopropylstyryl)isoquinoline
17. 6-Butyloxy-3,4-dihydro-1-(4-methylstyryl)isoquinoline
18. 6-Butyloxy-3,4-dihydro-1-(3,4-dimethoxystyryl)isoquinoline
19. 6-Butyloxy-3,4-dihydro-1-(4-nitrostyryl)isoquinoline
20. 6-Butyloxy-3,4-dihydro-1-(2,4-dimethylstyryl)isoquinoline
21. 6-Butyloxy-1-(2,4-dichlorostyryl)-3,4dihydroisoquinoline
22. 6-Butyloxy-1-(4-chlorostyryl)-3,4-dihydroisoquinoline
23. (E)-6-Butyloxy-1-(2-pentafluorophenyl)vinyl-3,4-dihydroisoquinoline
24. 6-Butyloxy-3,4-dihydro-1-(4-phenylstyryl)isoquinoline
25. 6-Butyloxy-1-(2,4-dichlorostyryl)-3,4-dihydro-7-methyl-isoquinoline
26. 3,4-Dihydro-1-(4-methylstyryl)-6-propyloxyisoquinoline
27. 1-(4-Cyanostyryl)-3,4-dihydro-6-propyloxyisoquinoline
28. 3,4-Dihydro-6-propyloxy-1-styrylisoquinoline
29. 3,4-Dihydro-1-(2,5-dimethoxystyryl)-6-propyloxyisoquinoline
30. 1-(4-Chlorostyryl)-3,4-dihydro-6-propyloxyisoquinoline
31. 1-(2,4-Dichlorostyryl)-3,4-dihydro-6-propyloxyisoquinoline
32. 3,4-Dihydro-1-(4-phenylstyryl)-6-propyloxyisoquinoline
33. 1-(2,4-Dichlorostyryl)-3,4-dihydro-6-(3,3-dimethylbutyloxy)isoquinoline
34. 1-(2-Chlorostyryl)-3,4-dihydro-6-(3,3-dimethylbutyloxy)isoquinoline
35. 1-(4-Chlorostyryl)-3,4-dihydro-6-(3,3-dimethylbutyloxy)isoquinoline
36. 6-Cyclohexylmethoxy-3,4-dihydro-1-styrylisoquinoline
37. 1-(4-Cyanostyryl)-6-cyclohexylmethoxy-3,4-dihydroisoquinoline
38. 1-(4-Chlorostyryl)-6-cyclohexylmethoxy-3,4-dihydroisoquinoline
39. 1-(2-Chlorostyryl)-6-cyclohexylmethoxy-3,4-dihydroisoquinoline
40. 1-(2,4-Dichlorostyryl)-6-cyclohexylmethoxy-3,4-dihydroisoquinoline
41. (E)-6-Cyclohexylmethoxy-1-(2-(pentafluorophenyl)vinyl)-3,4-dihydroisoquinoline
42. 1-(4-Chlorostyryl)-3,4-dihydro-6-(2-methylpropyloxy)-3-methylisoquinoline
43. 1-(2,4-Dichlorostyryl)-3,4-dihydro-3-methyl-6-(2-methylpropyloxy)isoquinoline
44. 1-(2-Chlorostyryl)-3,4-dihydro-3-methyl-6-(2-methylpropyloxy)isoquinoline
45. 6-(But-3-enyloxy)-1-(4-chlorostyryl)-3,4-dihydroisoquinoline
46. 6-(But-3-enyloxy)-1-(2,4-dichlorostyryl)-3,4-dihydroisoquinoline
47. 1-(2-Chlorostyryl)-3,4-dihydro-6-(2-methylpropyloxy)-isoquinoline
48. 1-(2,4-Dichlorostyryl)-3,4-dihydro-6-(2-methylpropyloxy)-isoquinoline
49. 1-(2,4-Dichlorostyryl)-3,4-dihydro-6-(3-methylbutyloxy)isoquinoline
50. 1-(4-Chlorostyryl)-3,4-dihydro-6-(3-methylbutyloxy)-isoquinoline
51. 1-(4-Chlorostyryl)-3,4-dihydro-6-(2-methylpropyloxy)-isoquinoline
52. 6-Benzyloxy-1-(4-cyanostyryl)-3,4-dihydroisoquinoline
53. 6-Benzyloxy-3,4-dihydro-1-styrylisoquinoline
54. 6-Benzyloxy-1-(2-chlorostyryl)-3,4-dihydroisoquinoline
55. 6-Benzyloxy-3,4-dihydro-1-(2,5-dimethoxystyryl)isoquinoline
56. 6-Benzyloxy-3,4-dihydro-1-(2,4-dimethoxystyryl)isoquinoline
57. 6-Benzyloxy-1-(4-chlorostyryl)-3,4-dihydroisoquinoline
58. 6-Benzyloxy-3,4-dihydro-1-(4-methylstyryl)isoquinoline
59. 6-Benzyloxy-3,4-dihydro-1-(4-isopropylstyryl)isoquinoline
60. 6-Benzyloxy-1-(4-t-butylstyryl)-3,4-dihydroisoquinoline 61. 6-Benzyloxy-3,4-dihydro-1-(2,4-dimethylstyryl)isoquinoline
62. 6-Benzyloxy-3,4-dihydro-1-(4-nitrostyryl)isoquinoline
63. 6-Benzyloxy-1-(2,4-dichlorostyryl)-3,4-dihydroisoquinoline
64. (E)-6-Benzyloxy-1-(2-(pentafluorophenyl)vinyl-3,4-dihydroisoquinoline
65. 1-(4-Chlorostyryl)-3,4-dihydro-6-phenoxy-isoquinoline
66. 1-(2,4-Dichlorostyryl)-3,4-dihydro-6-phenoxyisoquinoline
67. 6-(4-Chlorophenoxy)-1-(4-chlorostyryl)-3,4-dihydroisoquinoline
68. 6-(4-Chlorophenoxy)-3,4-dihydro-1-(4-nitrostyryl)-isoquinoline
69. 6-(4-Chlorophenoxy)-1-(2,4-dichlorostyryl)-3,4-dihydroisoquinoline
70. 6-(4-Chlorophenoxy)-3,4-dihydro-1-styrylisoquinoline
71. 6-(4-t-Butylphenoxy)-1-(2,4-dichlorostyryl)-3,4-dihydroisoquinoline
72. 6-(4-t-Butylphenoxy)-1-(4-chlorostyryl)-3,4-dihydroisoquinoline
73. 6-(4-t-Butylphenoxy)-3,4-dihydro-1-styrylisoquinoline
74. 6-Hexyloxy-3,4-dihydro-1-styrylisoquinoline
75. 1-(4-Cyanostyryl)-6-hexyloxy-3,4-dihydroisoquinoline
76. 1-(2-Chlorostyryl)-3,4-dihydro-6-hexyloxyisoquinoline
77. 1-(4-Chlorostyryl)-6-hexyloxy-3,4-dihydroisoquinoline
78. 1-(2,4-Dichlorostyryl)-6-hexyloxy-3,4-dihydroisoquinoline
79. 6-(4-t-Butylbenzyloxy)-1-(4-cyanostyryl)-3,4-dihydroisoquinoline
80. 6-(4-t-Butylbenzyloxy)-3,4-dihydro-1-styrylisoquinoline
81. 6-(4-t-Butylbenzyloxy)-1-(2,4-dichlorostyryl)-3,4-dihydroisoquinoline
82. 6-Benzyloxy)-1-(4-phenylstyryl)-3,4-dihydroisoquinoline
83. 6-(4-Chlorobenzyloxy)-3,4-dihydro-1-styrylisoquinoline
84. 6-(4-Chlorobenzyloxy)-1-(4-chlorostyryl)-3,4-dihydroisoquinoline
85. 6-(4-Chlorobenzyloxy)-1-(2,4-dichlorostyryl)-3,4-dihydroisoquinoline
86. 6-(2-Chlorobenzyloxy)-1-(4-cyanostyryl)-3,4-dihydroisoquinoline
87. 6-(2-Chlorobenzyloxy)-1-(2-chlorostyryl)-3,4-dihydroisoquinoline
88. 6-(2-Chlorobenzyloxy)-1-(2,4-dichlorostyryl)-3,4-dihydroisoquinoline
89. 6-(2,4-Dichlorobenzyloxy)-1-(4-cyanostyryl)-3,4-dihydroisoquinoline
90. 1-(4-Chlorostyryl)-6-(2,4-dichlorobenzyloxy)-3,4-dihydroisoquinoline
91. 6-(2,4-Dichlorobenzyloxy)-3,4-dihydro-1-styrylisoquinoline
92. 6-(2,4-Dichlorobenzyloxy)-1-(2,4-dichlorostyryl)-3,4-dihydroisoquinoline
93. 6-Benzyloxy-3,4-dihydro-1-(3,4,5-trimethoxystyryl)isoquinoline
94. 3,4-Dihydro-3-methyl-6-iso-propyloxy-1-styrylisoquinoline,
95. 3,4-Dihydro-6-ethoxy-3-propyl-1-styrylisoquinoline,
96. 3,4-Dihydro-3-ethyl-6-propyloxy-1styrylisoquinoline,
97. 1-(2-Chlorostyryl)-6-(3-trifluoromethyl benzyloxy)-3,4-dihydroisoquinoline
98. 1-(4-Cyanostyryl)-6-(3-trifluoromethyl benzyloxy)-3,4-dihydroisoquinoline
99. 3,4-Dihydro-1-styryl-6-(3-trifluoromethyl benzyloxy)isoquinoline
100. 6-Butyloxy-1-(2-fluorostyryl)-3,4-dihydroisoquinoline
101. 6-Benzyloxy-1-(2-fluorostyryl)-3,4-dihydroisoquinoline
102. (E)-6-Butyloxy-3,4-dihydro-1-[2-(4-bromo-2-thienyl)vinyl]isoquinoline
103. (E)-6-Butyloxy-3,4-dihydro-1-[2-(5-bromo-2-thienyl)vinyl]isoquinoline
104. (E)-6-Benzyloxy-3,4-dihydro-1-[2-(2-thienyl)vinyl]isoquinoline
105. (E)-6-Butyloxy-3,4-dihydro-1-[2-(2-thienyl)vinyl]isoquinoline
106. (E)-6-Benzyloxy-3,4-dihydro-1-(3-thienyl)vinyl isoquinoline
107. (E)-6-Butyloxy-3,4-dihydro-1-(3-thienyl)-vinylisoquinoline
108. (E)-6-Benzyloxy-3,4-dihydro-1-[2-(4-bromo-2-thienyl)vinyl]isoquinoline
109. (E)-6-Benzyloxy-3,4-dihydro-1-[2-(5-bromo-2-thienyl)vinyl]isoquinoline
110. (E)-6-Butyloxy-1-[2-(2-furyl)vinyl]-3,4-dihydroisoquinoline
111. (E)-6-Benzyloxy-1-[2-(2-furyl)vinyl]-3,4-dihydroisoquinoline
112. (E)-6-(4-Chlorobenzyloxy)-1-[2-(2-furyl)vinyl]-3,4-dihydroisoquinoline
113. (E)-3,4-Dihydro-6-propyloxy-1-[2-(5-nitro-2-furyl)]vinyl isoquinoline
114. (E)-6-Butyloxy-3,4-dihydro-1-[2-(5-nitro-2-furyl)]vinyl isoquinoline
115. (E)-6-Benzyloxy-3,4-dihydro-1-[2-(5-nitro-2-furyl)]vinyl isoquinoline
116. (E)-6-Butyloxy-3,4-dihydro-1-[2-(3-methyl-2-thienyl)vinyl]isoquinoline
117. (E)-3,4-Dihydro-1-[2-(3-methyl-2-thienyl)vinyl]-6-propyloxyisoquinoline
118. (E)-6-Benzyloxy-3,4-dihydro-1-[2-(3-methyl-2-thienyl)vinyl]isoquinoline
119. (E)-3,4-Dihydro-1-[2-(5-methyl-2-furyl)vinyl]-6-propyloxy-isoquinoline
120. (E)-6-Butyloxy-3,4-dihydro-1-[2-(5-methyl-2-furyl)vinyl]isoquinoline
121. (E)-6-Benzyloxy-3,4-dihydro-1-[2-(5-methyl-2-furyl)vinyl]isoquinoline
122. (E)-3,4-Dihydro-1-[2-(5-nitro-2-thienyl)vinyl]-6-propyloxyisoquinoline
123. (E)-6-Butyloxy-3,4-dihydro-1-[2-(5-nitro-2-thienyl)vinyl]isoquinoline
124. (E)-6-Butyloxy-3,4-dihydro-1-[2-(4-pyridyl)-vinyl]isoquinoline
125. (E)-6-Benzyloxy-3,4-dihydro-1-[2-(4-pyridyl)vinyl]isoquinoline
126. (E,E)-6-Benzyloxy-3,4-dihydro-1-(4-phenylbuta-1,3-dienyl)isoquinoline
127. (E,E)-3,4-Dihydro-1-(penta,-1,3-dienyl)-6-propyloxyisoquinoline
128. (E,E)-6-Butyloxy-3,4-dihydro-1-(penta-1,3-dienyl)isoquinoline 129. (E,E)-6-Hexyloxy-3,4-dihydro-1-(penta-1,3-dienyl)isoquinoline
130. (E,E)-6-Benzyloxy-3,4-dihydro-1-(penta-1,3-dienyl)isoquinoline
131. (E)-3,4-Dihydro-1-[2-(2-naphthyl)vinyl]-6-propyloxy-isoquinoline
132. (E)-6-Butyloxy-3,4-dihydro-1-[2-(2-naphthyl)vinyl]isoquinoline
133. (E)-6-Benzyloxy-3,4-dihydro-1-[2-(2-naphthyl)vinyl]isoquinoline
134. (E)-3,4-Dihydro-1-[2-(1-naphthyl)vinyl]-6-propyloxy-isoquinoline
135. (E)-6-Butyloxy-3,4-dihydro-1-[2-(1-naphthyl)vinyl]isoquinoline
136. (E)-6-Benzyloxy-3,4-dihydro-1-[2-(1-naphthyl)vinyl]isoquinoline
137. 3,4-Dihydro-1-prop-1-enyl-6-propyloxyisoquinoline
138. 6-Benzyloxy-3,4-dihydro-1-prop-1-enylisoquinoline
139. (E)-6-Butyloxy-3,4-dihydro-1-(penta-1,3-dienyl)isoquinoline
140. 6-Butyloxy-3,4-dihydro-1-(4-phenylbuta-1,3-dienyl)isoquinoline
141. 1-(2-(9-Anthryl)vinyl)-6-benzyloxy-3,4-dihydroisoquinoline,
142. 1-(2-(9-Anthryl)vinyl)-3,4-dihydro-6-propyloxy isoquinoline,
143. 3,4-Dihydro-1-(2-(9-phenanthryl)vinyl)-6-propyloxyisoquinoline,
144. 6-Butyloxy-3,4-dihydro-1-(2-(5-methyl-2-thienyl)vinyl)isoquinoline,
145. 3,4-Dihydro-1-(2-(5-methyl-2-thienyl)vinyl)-6-propyloxyisoquinoline,
146. 6-Benzyloxy-3,4-dihydro-1-(2-(5-methyl-2-thienyl)vinyl)isoquinoline,
147. (Z)-6-Butyloxy-1-(1-bromo-2-phenylvinyl)-3,4-dihydroisoquinoline
148. (Z)-6-Benzyloxy-1-(1-bromo-2-phenylvinyl)-3,4-dihydroisoquinoline
149. (Z)-6-Butyloxy-1-(1-fluoro-2-phenylvinyl)-3,4-dihydroisoquinoline
150. (Z)-6-Butyloxy-1-(1-chloro-2-phenylvinyl-3,4-dihydroisoquinoline
151. (Z)-6-Benzyloxy-1-(1-chloro-2-phenylvinyl)-3,4-dihydroisoquinoline
152. (E)-6-Benzyloxy-3,4-dihydro-1-(2-phenyl)-1-methylvinyl)isoquinoline
153. (E)-6-Butyloxy-3,4-dihydro-1-(2-phenyl-1-methylvinyl)isoquinoline
154. (Z)-6-Benzyloxy-1-(1-fluoro-2-phenylvinyl)-3,4-dihydroisoquinoline
155. 1-(2,4-Dichlorostyryl)-3,4-dihydro-6,7-dipropyloxyisoquinoline
156. 1-(4-Chlorostyryl)-3,4-dihydro-3-methyl-6,7-dipropyloxyisoquinoline
157. 6,7-Dibutyloxy-1-(4-chlorostyryl)-3,4-dihydroisoquinoline
158. 1-(2,4-Dichlorostyryl)-3,4-dihydro-3-methyl-6,7-dipropyloxyisoquinoline
159. 6,7-Dibutyloxy-1-(4-chlorostyryl)-3-methylisoquinoline
160. 6-Butyloxy-1-(2,4-dichlorostyryl)-7-ethoxy-3,4-dihydroisoquinoline
161. 7-Butyloxy-1-(2,4-dichlorostyryl)-6-ethoxy-3,4-dihydroisoquinoline
162. 7-Butyloxy-1-(4-chlorostyryl)-6-ethoxy-3,4-dihydroisoquinoline
163. 6-Butyloxy-1-(4-chlorostyryl)-7-ethoxy-3,4-dihydroisoquinoline
164. 1-(4-Chlorostyryl)-3,4-dihydro-6,7-dipentyloxyisoquinoline
165. 1-(4-Chlorostyryl)-6,7-dihexyloxy-3,4-dihydroisoquinoline
166. 3,4-Dihydro-1-(4-hydroxystyryl)-6,7-dipropyloxyisoquinoline
167. 3,4-Dihydro-1-(4-trifluoromethylstyryl)-6,7-dipropyloxyisoquinoline
168. 1-(4-Chlorostyryl)-3,4-dihydro-6,7-dipropyloxy isoquinoline
169. 6,7-Bisbenzyloxy-1-(2-Chlorostyryl)-3,4-dihydroisoquinoline
170. 6,7-Bisbenzyloxy-1-(2,4-dichlorostyryl)-3,4-dihydroisoquinoline
171. 5,6-Bis(benzyloxy)-3,4-dihydro-1-styrylisoquinoline
172. 5,6-Bis(benzyloxy)-1-(4-chlorostyryl)-3,4-dihydroisoquinoline
173. 5,6-Bis(benzyloxy)-1-(2,4-dichlorostyryl)-3,4-dihydroisoquinoline
174. 5-Benzyloxy-3,4-dihydro-8-methoxy-1-styrylisoquinoline
175. 5-Benzyloxy-1-(4-cyanostyryl)-3,4-dihydro-8-methoxyisoquinoline
176. 6-Benzyloxy-1-(4-chlorostyryl)-3,4-dihydro-7-methoxy-5-propylisoquinoline
177. 6-Benzyloxy-1-(2-chlorostyryl)-3,4-dihydro-7-methoxy-5-propylisoquinoline
178. 6-Hydroxy-3,4-dihydro-7-methoxy-5-propyl-1-styrylisoquinoline
179. 1-(2,4-Dichlorostyryl)-3,4-dihydro-6-hydroxy-7-methoxy-5-propylisoquinoline
180. 1-(2-Chlorostyryl)-3,4-dihydro-6-hydroxy-7-methoxy-5-propylisoquinoline
181. 1-(4-Chlorostyryl)-3,4-dihydro-5-hydroxy-8-methoxyisoquinoline
182. 6-Butyloxy-1-(2,4-dichlorostyryl)-3,4-dihydro-7-methylisoquinoline
183. 1-(4-Acetoxystyryl)-3,4-dihydro-6,7-dipropyloxy isoquinoline
184. 1,2,3,4-Tetrahydro-6,7-dibutyloxy-1-(4-chlorostyryl)isoquinoline
185. 1-(4-Chlorostyryl)-1,2,3,4-tetrahydro-6,7-dipropyloxy isoquinoline
186. 3,4-Dihydro-3,3-dimethyl-6-propyloxy-1-styrylisoquinoline,
187. 3,4-Dihydro-3,3,4,4-tetramethyl-6-propyloxy-1-styrylisoquinoline,
188. 6-Butyloxy-3,4-dihydro-3,3-dimethyl-1-styrylisoquinoline,
189. 3,4-Dihydro-3,3-dimethyl-6-heptyloxy-1-styrylisoquinoline,
190. 3,4-Dihydro-4,4-dimethyl-6-propyloxy-1-styrylisoquinoline,
191. 4-Butyloxystyryl-3,4-dihydroisoquinoline,
202. 6-Butyloxy-3,4-dihydro-1-[2-(3,4-dihydro-5,6,7-trimethoxynaphthyl)]isoquinoline
203. 6-Benzyloxy-3,4-dihydro-1-[3,4-dihydro-5,6,7-trimethoxy-2-naphthyl)]isoquinoline or salts or acyl derivatives thereof.

The most preferred compound of the present invention is (E)-1-(2-Cyclohexylvinyl)-3,4-dihydro-6-propyloxy isoquinoline and its salts, particularly preferred salts being these formed with phosphoric acid.

Compounds of the formula (III) to (XII) exist in a number of isomeric forms. The present invention provides mixtures of the isomeric forms as well as the individual isomers.

Thus the compounds of the present invention may exist in either the E or Z isomeric forms with reference to the vinyl double bond. The E-isomers are generally preferred; the exceptions being those compounds wherein the vinyl double bond is trisubstituted and the third substituent is nitro, trifluoromethyl or halogen, in which cases the Z-isomers are preferred.

When the compound is of the formula (III) to (VII) and is substituted at the 3-and/or 4-positions, it may exist in optical isomeric forms with respect to these positions, and when the compound is tetrahydroisoquinoline, it may also exist in optical isomeric forms with respect to the 1-position of the isoquinoline ring.

The substituents hereinbefore defined may also contain assymetric centres thereby imparting optical activity to the compound. All optical forms are within the scope of the present invention.

Suitably the compounds of the formula (III) to (XII) are present in the form of the free base or an acid addition salt thereof. Suitable acid addition salts of the compounds of the formulae (III) to (XI) include those formed with both organic and inorganic acids.

Thus, suitable salts include those formed from hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic and glucuronic acids. Most preferably, the acid addition salts will be pharmaceutically acceptable.

When the compounds of the formulae (III) to (XII) are substituted by hydroxy groups, alkali metal salts of these compounds may be formed and these salts also comprise part of the present invention. Particularly suitable alkali metal salts are those formed with sodium and potassium.

Suitable acyl derivatives are those wherein a hydroxy group is substituted by a group —COM— wherein M is hydrogen or a group $R^{24}$ as hereinbefore defined. When the compounds of the formula (III) are 1, 2, 3, 4-tetrahydroisoquinolines, they form acyl derivatives wherein the group —COM is attached to the nitrogen atom in the 2-position of the isoquinoline ring.

In another aspect, the present invention provides a method for the treatment or prophylaxis of a protozoal infection, particularly a trichomonal infection, by the administration of an effective non-toxic antiprotozoal amount of a compound of the formula (III) or a pharmaceutically acceptable salt thereof, or a composition as hereinafter described.

The present invention also provides a method for the treatment or prophylaxis of fungal infections in man or animals, comprising the administration of an effective non-toxic antifungal amount of a compound of the formula (IIIA) as hereinbefore defined.

Whilst it is possible for a compound of the formula (III) to be administered alone as the raw chemical, it is preferable to present the compound of formula (III) as a pharmaceutical formulation.

The exact method of administration to be used ultimately will be at the discretion of the physician treating the condition and will depend upon the particular nature of the infection being treated. However, it has been found most convenient to administer the compounds of the formulae (III) or (IIIA) topically.

Accordingly in another aspect, the present invention provides a topical formulation, comprising a compound of the formula (III) or a salt or acyl derivative thereof in admixture with one or more pharmaceutically acceptable carriers or excipients. The formulation may take the form of an ointment, cream, suspension, lotion, powder, solution, paste, gel, spray, aerosol or oil.

Alternatively, a formulation may comprise a pessary or a suppository or dressings such as bandages and adhesive plasters impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

The active ingredient is generally present in a concentration of between 0.1 and 95% w/w of the composition and preferably is present at a concentration of 0.1–5%.

Formulations particularly suitable for rectal and vaginal administration suitably are presented as unit-dose suppositories or pessaries. These may be prepared by admixture of the active ingredient with one or more conventional solid carriers, for example coca butter, and shaping the resulting mixture. Alternatively, in the case of vaginal administration, the formulation may be presented as a tampon impregnated with the active ingredients and optionally one or more excipients or diluents. Other formulation suitable for rectal and vaginal administration include creams, gels, foams, pastes and sprays.

The frequency of administration of the composition, the amount of compound administered and the duration of the treatment will of course all vary according to the severity of the infection or condition. Ultimately the treatment regimen will be at the discretion of the physician.

Typically, pessaries will be inserted into the vagina singly or in twos or threes, generally once or twice daily. It is often convenient to administer pessaries nightly. Vaginal creams, gels, foams or ointments will generally be administered one to four times daily and, similarly, it may be found convenient to apply the medicament at night. Application of a cream is often assisted by means of an applicator.

Often, a cream will be administered in conjunction with another form of the medicament, for example, a tampon or pessary. Combinations such as these are within the scope of the present invention.

Tampons will usually be administered once daily although in certain cases it may prove necessary to increase the frequency of administration.

The duration of treatment generally will be between one and fourteen days although longer periods may be required in some instances.

As mentioned above, the quantity of active compound administered daily will depend upon the severity of the infection but typically it will vary between 10 mg and 1 g. Most conveniently the quantity of active compound administered will vary between 20 mg and 500 mg daily.

Although topical formulations are preferred, compounds of the present invention may also be administered by other routes e.g. orally or parenterally. Thus, in a further aspect, the present invention provides a pharmaceutical composition comprising a novel compound of the formula (III) in combination with a pharmaceutically acceptable carrier. By the terms "pharmaceutical composition" and "pharmaceutically acceptable carrier" are meant those compositions and carriers suitable for use in human and/or veterinary medicine. The pharmaceutically acceptable carriers present in the compositions of the present invention are materials recommended for the purpose of administering the medicament. These may be liquid, solid or gaseous materials, which are otherwise inert or medically acceptable and are compatible with the active ingredients.

These pharmaceutical compositions may be given parenterally, used as a suppository or pessary or applied topically as an ointment, cream or powder.

For oral administration, fine powders or granules will contain diluting, dispersing and/or surface active agents, and may be presented in a draught, in water or in a syrup, in capsules, cachets or tablets in the dry state or in a non-aqueous suspension in water or syrup. Where desirable or necessary, flavouring, preserving, suspending, thickening or emulsifying agents can be included.

For parenteral administration, the compounds may be presented in sterile aqueous injection solutions which may contain antioxidants, buffers and other pharmaceutically acceptable additives where necessary.

Other ingredients which may be included in compositions comprising novel compounds of the formula (III) include medically inert ingredients such as solid or liquid diluents e.g. lactose, glucose, starch or calcium phosphate for tablets or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers and antioxidants which are useful as carriers in such formulations.

For application to plants, or plant products such as timber, compounds of the formula (IIIa) typically are formulated as dusts or powders or as solutions or suspensions for spraying, dipping or painting on to the plant or plant product, the formulations being prepared according to methods well known in the art of plant and plant product protection.

Where desired the formulations can be presented as concentrates, e.g. powders and liquid concentrates, for dilution to the appropriate strength. The formulations optionally may contain other fungicides and/or preservatives, insecticides, dyes, solvents and diluents. For the treatment of timber, particularly suitable methods of administering the compounds of the formula (IIIa) include dipping, painting or vacuum impregnation of the timber.

The antifungal activity of the compounds of the present invention may be evaluated by determining the minimum fungistatic (inhibition) concentration (m.i.c.). This test is usually performed by preparing a series of plates or tubes containing a suitable nutrient medium, each plate or tube also containing a different concentration of the test compound and then inoculating the medium with the fungal species. After an incubation period the plates are examined visually for the presence or absence of fungal growth. The m.i.c. is the minimum concentration required to prevent fungal growth.

The antiprotozoal e.g. antitrichomonal, activity of the compounds of the present invention may be assessed by conventional methods, for example by determining the minimum inhibition concentration (m.i.c.) or 50% inhibition level ($IC_{50}$).

It follows from the above that many of the compounds of the present invention are active against both trichomonads and fungi and, indeed, those compounds exhibiting such dual activity represent a preferred embodiment of the present invention.

In addition, many of the compounds are also active against other parasitic organisms, for example filarial worms such as *Brugia pahanga* and *Nippostrongylus brasiliensis*.

It has also been found that compounds of the formula (III) have activity against anaerobic or substantially anaerobic bacteria such as *Gardnerella vaginalis*, the species now known to be responsible for many of the conditions hitherto classified as non-specific vaginitis, *B. fragilis*, *Cl. difficile* and *Fuso. nucleatum* certain compounds of the formula (III) additionally have insecticidal activity, for example activity against mosquito larvae and clothes moth and carpet beetle larvae.

The present invention also provides processes for the preparation of novel compounds of the formula (III) which processes comprise:

(a) the cyclisation of a compound of the formula (XIII)

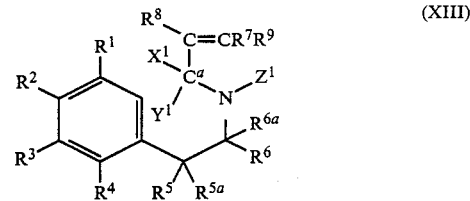

wherein $R^1$–$R^7$ are as hereinbefore defined, and either $Z^1$ is hydrogen and $X^1$-C-$Y^1$ is a group C=O, or $X^1$ is a leaving group and $Y^1$ and $Z^1$ together form a second bond between $C_a$ and N.

(b) when it is desired to prepare a novel compound of the formula (III) in which $R^7$ is hydrogen and $R^8$ is hydrogen, $C_{1-2}$ alkyl, cyano or nitro, the condensation of a compound of the formula (XIV) wherein $R^1$–$R^6$ are as hereinbefore defined and $R^{8a}$ and $R^{8b}$ are either both hydrogen or together form a group=P(O Alkyl)$^2$ or =PPh$_3$, with a compound of the formula (XV) wherein $R^7$ and $R^9$ are as hereinbefore defined.

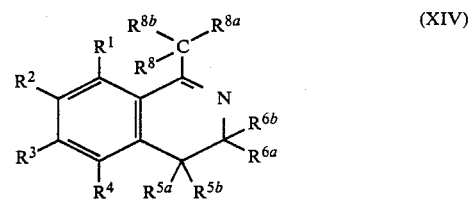

(c)
(i) When it is desired to prepare a novel compound of the formula (III) wherein both $R^{6a}$ and $R^{6b}$ are $C_{1-4}$ alkyl groups; the reaction of a compound of the formula (XVI)

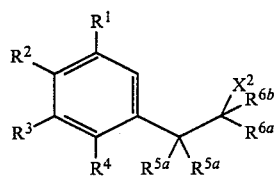
(XVI)

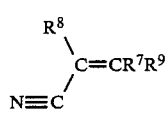
(XVII)

with a compound of the formula (XVII) wherein $R^1$–$R^5$ and $R^7$–$R^9$ are as hereinbefore defined, $R^{6a}$ and $R^{6b}$ are the same or different and each is a $C_{1-4}$ alkyl group and $X^2$ is a leaving group.

(ii) When it is desired to prepare a novel compound of the formula (III) wherein $R^{6b}$ is a group $CH_2R^{6c}$ and $R^{6c}$ is hydrogen or $C_{1-3}$ alkyl, the reaction of compound of the formula (XVIa):

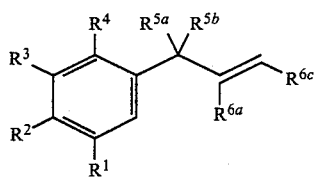
(XVIa)

with a compound of the formula (XVII).

(d) the cyclisation of a compound of the formula (XVIII)

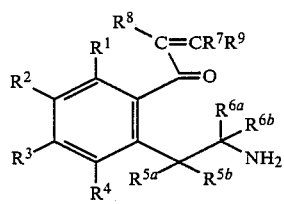
(XVIII)

where in $R^1$–$R^9$ are as hereinbefore defined.

(e) the conversion of one novel compound of the formula (III) into another novel compound of the formula (III)

(a) The cyclisation of a compound of the formula (XIII) wherein Z is hydrogen and X-C-Y is a group C═O, which is known to those skilled in the art as a Bischler-Napieralski reaction, is usually carried out by reacting the compound (XIII) with a dehydrating agent in the presence of an inert solvent, for example according to the conditions described in *Organic Reactions*, 1951, vol. VI, 74 or British Patent No. 1,181,959. Typically the solvent is a hydrocarbon such as benzene, toluene, xylene, cymene, decalin or tetralin, an inert polar aprotic solvent such as nitrobenzene or a halogenated hydrocarbon such as chloroform, carbon tetrachloride, 1,2-dichloroethane chlorobenzene, dichlorobenzene, trichlorobenzene or brominated alkenes. Preferably the solvent is chloroform or toluene. When the dehydrating agent is a liquid, e.g. phosphorus oxychloride, the reaction may, if so desired, be carried out in the neat reagent. The condensing or dehydrating agent is usually chosen from phosphorus pentoxide, phosphorus oxychloride, polyphosphoric acid, ethyl polyphosphate, phosphorus pentachloride, aluminium chloride, stannic chloride, thionyl chloride, zinc chloride, aluminium oxide, phosphorus oxybromide, trifluoroacetic acid, optionally in the presence of trifluoroacetic anhydride, and silicon tetrachloride. It has been found convenient to employ a phosphorus based reagent as the dehydrating agent; preferably the reagent is phosphorus oxychloride or phosphorus pentoxide or mixtures thereof.

The cyclisation typically takes place at temperatures between 0° C. and 206° C. and conveniently is carried out between 55° C. and 120° C.

Compounds of the formula (XIII) wherein Z is hydrogen and X-C-Y is a group C═O are prepared by reacting amines of the formula (XIX)

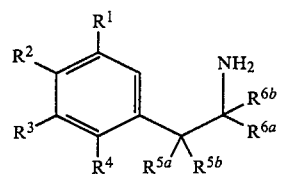
(XIX)

wherein $R^1$–$R^{6b}$ are as hereinbefore defined, with carboxylic acids of the formula (XX)

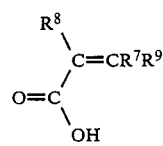
(XX)

or functional derivatives thereof such as acid halides, esters, amides or anhydrides, wherein $R^7$–$R^9$ are as hereinbefore defined.

Acylation of the amines of the formula (XIX) will take place under a wide range of conditions well known to those skilled in the art, for example see U.S. Pat. No. 3,823,148.

Amines of the formula (XIX) may be synthesised according to methods well known to those skilled in the art.

It was found particularly convenient to prepare amines of the formula (XIX) wherein $R^3$ is $R^{24}O$ and $R^{24}$ is as hereinbefore defined, according to the route described in schemes 1 and 2 below.

Scheme 1
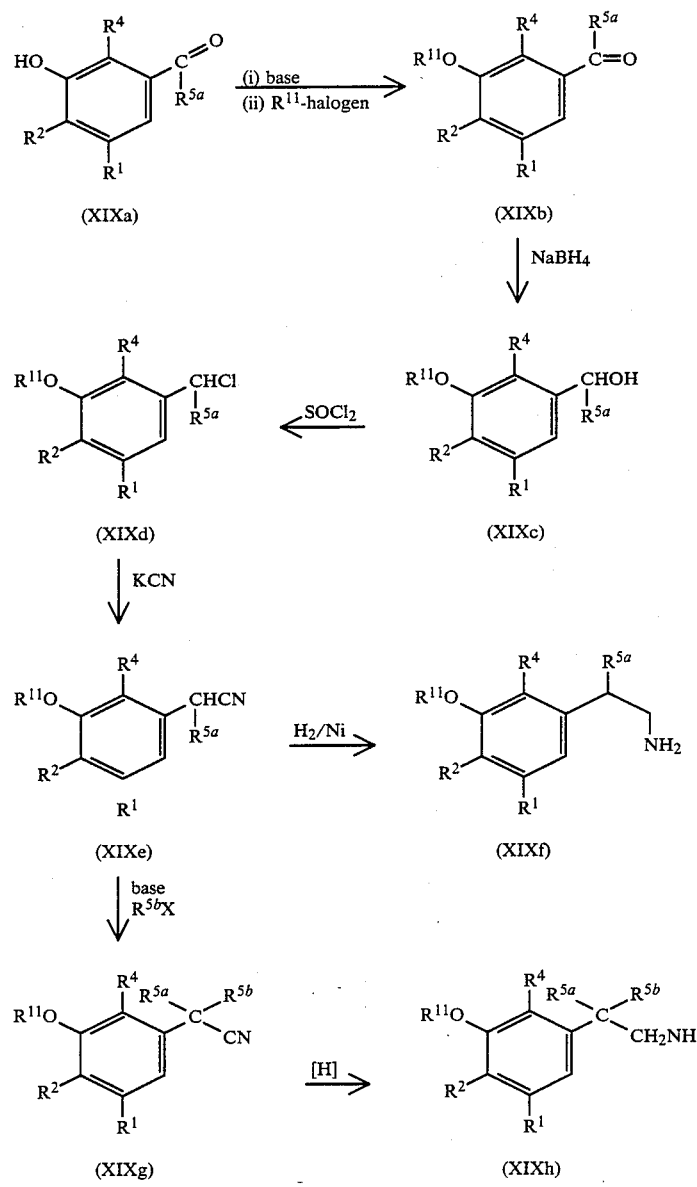
Scheme 2
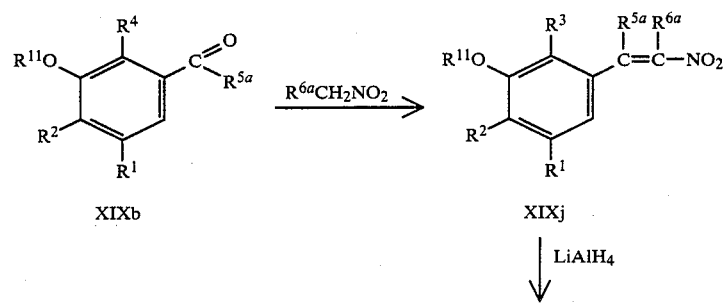

Scheme 2

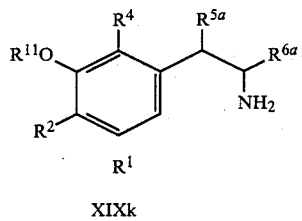

XIXk (b) The reaction of compounds of the formula (XIV), wherein $R^{8a}$ and $R^{8b}$ are hydrogen, with compounds of the formula (XV) takes place under conditions similar to those described in *Izv. Akad. Nauk. Arm. SSR Khim. Nauki* 17(5), 5 62–6 (1964) (Russ) (C.A. 62, 11778d) or *C. R. Hebd. Seances Acad. Sci., Ser., C.* 1978, 286 (24), 675–7 (CA 89:163618j).

Thus, for example the reactants may simply be stirred together in the presence of an acylating agent such as acetic anhydride. Alternatively, the reaction may be carried out under basic conditions, for example the 1-methyl group may be lithiated and the lithio-derivative subsequently treated with an aldehyde or ketone.

Compounds of the formula (XIV) wherein $R^{8a}$ and $R^{8b}$ are hydrogen may be prepared by means of the Bischler-Napieralski reaction of a compound of the formula (XXI):

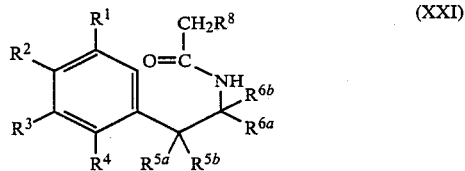

(XXI)

wherein $R^1$–$R^6$ and $R^8$ are as hereinbefore defined.

Compounds of the formula (XIV) wherein $R^{8a}$ and $R^{8b}$ together constitute a group:

O=P-(O Alkyl)$_2$ or =PPh$_3$ may be prepared and reacted with carbonyl compounds of the formula (XV) under conditions analogous to those well known to the man skilled in the art of Wittig and related reactions, see for example E. C. Taylor and S. F. Martin, *J. Amer. Chem. Soc.*, 1972, 94, 2874, A. Buzas and J. P. Finet, *Tetrahedron Letters*, 1976, 2433 and N. Whittaker, *J. Chem. Soc. (C)*, 1969, 94. Thus the reactions are suitably carried out in an anhydrous solvent inert to the reaction conditions employed, for example toluene, benzene, tetrahydrofuran, dioxan, dimethylsulphoxide, glycol ethers and $C_{1-6}$ alkyl ethers, in the temperature range $-80°$ C. to $160°$ C. The reaction is conveniently carried out between $0°$ C. and $50°$ C. and most conveniently is carried out at room temperature.

Compounds of the formula (XIV) wherein $R^{8a}$ and $R^{8b}$ together form a group O=P-(O Alkyl)$_2$ or =PPh$_3$ typically are prepared by reacting a compound of the formula (XIX)

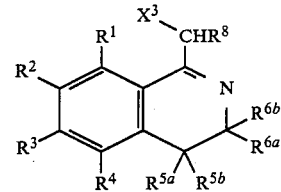

(XXII)

wherein $R^1$–$R^6$ are as hereinbefore defined and $X^3$ is chlorine, bromine or iodine, with triphenylphosphine or a trialkylphosphite, followed by treatment of the resulting phosphonium salt with a strong base such as dimsyl sodium or a $C_{1-4}$ alkyl or aryllithium compound such as butyl lithium, a metal hydride such a sodium hydride or an alkali metal amide such as sodamide in an anhydrous solvent as hereinbefore defined. Compounds of the formula (XXII) may be prepared by Bischler-Napieralski cyclisation of an α-halo acetyl derivative of a phenethylamine of the formula (XVI) as hereinbefore defined, for example under conditions analogous to those described by Buzas and Finet (idem) or by R. Child and F. L. Pyman, *J. Chem. Soc.*, 1931, 41.

(c) The reaction of compounds of the formula (XVI), when $X^2$ is halogen, with compounds of the formula (XVII) are generally carried out in a suitable solvent and in the presence of a metal halide such as stannic chloride or aluminium chloride, for example according to conditions similar to those described in *Chem. Ber.*, 1961, 94, 199.

When $X^2$ is hydroxy, the reaction will usually be carried out in the presence of a strong acid such as perchloric, phosphoric, polyphosphoric, formic or substituted sulphonic acid or boron trifluoride, and preferably the acid is sulphuric acid. If desired a co-solvent or diluent can be employed. Suitable co-solvents include glacial acetic acid, acetic anhydride, di-n-butyl ether, chloroform, carbon tetrachloride, nitrobenzene and hexane. The reaction generally will be carried out in the temperature range $0°$–$100°$ C., and preferably in the range $20°$–$55°$ C. In general the conditions employed in this reaction will be similar to those described for analogous processes in *Organic Reactions* Vol. 17, 213.

It has additionally been discovered that when $X^2$ is hydroxy, the reaction can be carried out in the presence of trifluoroacetic acid/trifluoroacetic anhydride (TFA/TFAA) at approximately ambient temperature.

Compounds of the formula (XVII) wherein $X^2$ is hydroxy can be prepared by reaction of the corresponding ester with two equivalents of an alkyl Grignard reagent, for example methyl magnesium iodide. The ester can be obtained via known hydrolysis/esterification procedures from compounds of the formula (X1Xe) or (X1Xg).

(d) The cyclisation of a compound of the formula (XVIII) will take place under conditions analogous to those disclosed in U.S. Pat. No. 3,067,203 and U.K. Patent No. 862,052 for example by heating in the presence of an acidic reagent such as a mineral acid or phosphorus oxychloride, optionally in the presence of an organic solvent such as benzene, toluene or acetic acid. Preparation of compounds of the formula (XVIII) can be achieved by condensing an aldehyde of the formula (XV) as hereinbefore defined, with a compound of the formula (XXIII).

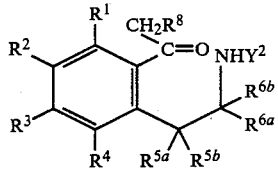

wherein $R^1$–$R^6$ and $R^8$ are as hereinbefore defined and $Y^2$ is the acyl residue of a carboxylic acid e.g. acetyl. Condensation takes place in the presence of a base such as an alkali metal amide, alkoxide or hydroxide, in a solvent such as tetrahydrofuran, dioxan, or a $C_{1-4}$ alcohol or aqueous mixtures thereof. The compounds of the formula (XXIII) are synthesised according to methods analogous to those described in U.S. Pat. No. 3,067,203.

(e) The conversion of one novel compound of the formula (III) into another novel compound of the formula (III) will be carried out according to methods well known to those skilled in the art. For example, when such a compound is substituted by a hydroxy or thio group, this may be acylated or alkylated according to known methods. When the compound of the formula (III) is substituted by acyloxy or benzyloxy, this may be transformed into hydroxy by hydrolysis or hydrogenolysis respectively. When a thio or hydrocarbylthio substituent is present, this may, if desired, be replaced by a hydrogen atom through hydrogenolysis. When a compound of the formula (III) is a tetrahydroisoquinoline, this may, if desired, be oxidised to the 3,4-dihydroisoquinoline according to known methods. It will be readily apparent to the skilled man that such methods will not be employed if the compound possesses additional groups which it is desired should be retained in the compound but which are sensitive to the aforementioned conditions. Novel chemical intermediates of the formula (XIII), (XV), (XVI), (XVIa), (XVIII), (XIX), (XXI), (XXII) and (XXIII) are within the scope of the present invention.

The following examples illustrate the invention but are not intended to limit it in any way.

EXAMPLE 1

(E)-6-Butyloxy-1-(2-cyclohexylvinyl)-3,4-dihydroisoquinoline nitrate 1A. 3-Butyloxybenzaldehyde 3-Hydroxybenzaldehyde (61 g) was added over 40 minutes to a suspension of sodium hydride (13.0 g) in dimethylformamide (700 cm³), the temperature of the reaction mixture being kept below 10° C. by means of a CO₂/oxitol bath. After stirring for 35 minutes, 1-bromobutane (73 g) was added dropwise over one hour and the mixture was then stirred at room temperature for 2.5 hours followed by heating at 85° C. for a further 2.5 hours. The resulting mixture was poured into ice water (1000 cm³) and was allowed to stand overnight before extracting with 40°–60° petrol/ether (3:1) (5×200 cm³). The combined organic layers were washed with 1M sodium hydroxide solution containing sodium chloride, dried over sodium sulphate, treated with activated charcoal, filtered and then evaporated down to give a golden brown mobile oil (79.7 g).

1B. 3-Butyloxybenzylalcohol

The product of Example 1A (79.7 g) was dissolved in methanol (550 cm⁵) and to the cooled stirred solution was added sodium borohydride (17.45 g). After stirring at room temperature for 150 minutes the mixture was filtered and evaporated to dryness. The residue was partitioned between water (500 cm⁵) and ether (200 cm⁵) and the aqueous layer was separated and further extracted with ether (4×200 cm⁵). The combined ether extracts were washed with water, dried, treated with activated charcoal, filtered and then evaporated down to give a golden oil (78.7 g).

1C. 3-Butyloxybenzylchloride

The product of Example 1B (78.7 g) in ether (450 cm⁵) was treated with thionyl chloride (85 cm⁵) and pyridine (6 drops) in dry ether (4 cm³) and following addition, the reaction mixture was heated at reflux for 3 hours. After allowing to cool the mixture was filtered and evaporated and the residue was partitioned between water (600 cm³) and ether (200 cm³). The aqueous phase was separated and further washed with ether (4×200 cm³) and the combined ether extracts were washed with distilled water followed by 5% sodium bicarbonate solution before drying, filtering and evaporating down to a tan mobile oil (83.7 g).

1D. 3-Butyloxybenzylcyanide

The product of Example 1C (42.0 g) in dimethylsulphoxide (200 cm³) was added to a suspension of potassium cyanide (22.4 g) in dimethylsulphoxide (300 cm³) and the mixture was stirred at room temperature for 3 days before being allowed to stand for a further 3 days. The mixture was then diluted with water and was extracted with ether (5×200 cm³); the combined ether extracts were washed with distilled water, dried, treated with activated charcoal, filtered and evaporated down to give the title compound as a tan mobile oil (38.6 g).

1E. 2-(3-Butyloxyphenyl)ethylamine

The nitrile from Example 1D (38.64 g) was dissolved in methanol (700 cm³) saturated with ammonia and the resulting mixture was hydrogenated at 70° C. and 45 atmospheres of hydrogen over Raney nickel catalyst for 2 hours. After cooling the solution was filtered and evaporated to give a green oil (42.2 g). The green oil was distilled under reduced pressure and the product fraction was collected at 104°–110°/0.05 mm Hg (28.2 g).

1F. N-[3-Cyclohexylpropenoyl]-m-butoxyphenethylamine

Powdered potassium carbonate (4.5 g) was added to a solution of 2-(3-butyloxyphenyl)ethylamine (4.12 g) in acetonitrile (55 cm³). A solution of 3-cyclohexylacryloyl chloride (3.66 g) in acetonitrile (20 cm³) was added dropwise over fifteen minutes and the reaction mixture was then stirred at room temperature for 2 hours. Following treatment with distilled water (75 cm³) and SVM (3 cm³), a white precipitate was formed. This was filtered off and sucked dry to give the product (3.76 g) m.p. 67°–71° C.

1G. 6-Butyloxy-1-[2-cyclohexylethenyl]-3,4-dihydroisoquinoline nitrate, one quarter hydrate To a solution of the product from Example 1G (4.6 g) in dry ethanol-free chloroform (40 cm$^3$) was added phosphoryl chloride (5 cm$^3$). The resulting mixture was heated at reflux for 5.5 hours before evaporating the solvent to leave a pale tan mobile oil. The oil was treated with water (30 cm$^3$), stirred vigorously for 20 minutes and then cooled to 2° C. before running off the aqueous phase. The oil was then dissolved in acetone (10 cm$^3$), ether was added and the solution was extracted twice with saturated potassium bicarbonate solution (50 cm$^3$). The aqueous layer was then extracted once with ether (50 cm$^3$) and the combined ether extracts were dried over sodium sulphate, filtered and then added to a cold stirred solution of 70% nitric acid (1.25 g) in ethyl acetate (20 cm$^3$). The title compound crystallised out as pale cream plates (2.06 g) m.p. 160°–161° C.

Analysis calculated for $C_{21}H_{29}NO.HNO_3.0.25\ H_2O$: C, 66.58; H, 8.06; N, 7.39; Found; C, 66.65; H, 8.02; N, 7.30

EXAMPLE 2

6-Benzyloxy-1-[2-cyclohexylethenyl]-3,4-dihydroisoquinoline nitrate

2A. N-[3-Cyclohexylpropenoyl]-2[3-benzyloxyphenyl]ethylamine

To a solution of 2-[3-benzyloxyphenyl]ethylamine (2.3 g) (prepared in a manner analogous to that described in Example 1E) in acetonitrile (25 cm$^3$) was added powdered potassium carbonate (2.1 g) followed by 3-cyclohexylpropenoyl chloride (1.72 g) in acetonitrile (10 cm$^3$) which was added over ten minutes. The resulting mixture was stirred for one hour and was then treated with water (40 cm$^3$) and SVM (3 cm$^3$) thereby causing the precipitation of an oil which solidified to give a pale tan solid after several minutes. This solid was filtered off, washed with 5% SVM in water and sucked dry. Yield=3.08 g m.p. 98°–100° C.

2B. 6-Benzyloxy-1-[2-cyclohexylethenyl]-3,4-dihydroisoquinoline nitrate

To a solution of the amide (1.0 g), obtained from Example 2A, in sodium dried toluene (10 cm$^3$) at reflux was added phosphoryl chloride (1.2 cm$^3$), and the resulting reaction mixture was heated at reflux for fifteen minutes before evaporating to dryness. The residue was treated with distilled water (10 cm$^3$), stirred well and was then allowed to stand at 2° C. The aqueous phase was decanted off, the residue was dissolved in a minimum quantity of SVM and the resulting solution was partitioned between ether and saturated potassium bicarbonate solution. The ether layer was separated, extracted a further two times with potassium bicarbonate solution, dried over sodium sulphate, filtered and was then added to a cold solution of nitric acid (0.26 g) in ethyl acetate (6 cm$^3$) whereupon, with stirring, a gum separated out. Treatment of the gum with ethyl acetate, acetone and ether resulted in crystallisation of the title compound as beige prisms (0.25 g) m.p. 151°–152° C. Analysis: Calculated for: $C_{24}H_{27}NO.HNO_3$: C, 70.59; H, 6.86; N, 6.86; Found: C, 70.46; H, 6.71; N, 6.92.

EXAMPLE 3

6-Butyloxy-3,4-dihydro-1-styrylisoquinoline hydrochloride 3A. 2-[3-Butyloxyphenyl]-1-nitroethene The product of Example 1A (5.0 g) was dissolved in glacial acetic acid (18 cm$^3$) and nitromethane (2.1 g) and ammonium acetate (0.97 g) were added. The reaction mixture was heated at reflux for 10 hours, further nitromethane (0.5 g) being added after 4 hrs of refluxing. The reaction mixture was then treated with a methanol/water mixture (1:2) (40 cm$^3$) and extracted several times with ether. The combined ether extracts were washed successively with water and potassium bicarbonate solution, dried over sodium sulphate, treated with activated charcoal, filtered and then evaporated down to give a dark brown oil (5.4 g).

3B. 2-[3-Butyloxyphenyl]ethylamine

Lithium aluminum hydride (25.0 g) was added carefully to sodium dried tetrahydrofuran (THF) (250 cm$^3$) at 0° C. Sodium dried ether (250 cm$^3$) was then added via a pressure equalising dropping funnel and this was followed by the dropwise addition of a solution of the product of Example 3B (48.7 g) in sodium dried ether (2500 cm$^3$) over 2 hours, the reaction mixture being maintained at approximately 10° C. throughout. The reaction mixture was allowed to warm to room temperature and was then stirred at this temperature for 1± hours before heating under reflux for a further 1.5 hours. After cooling the reaction mixture to 0° C., ether (250 cm$^3$) was added followed by the careful addition of 5M sodium hydroxide. Following dilution of the mixture with water (200 cm$^3$), the organic phase was separated and the aqueous layer was further washed with ether (4×200 cm$^3$). The combined ether extracts were dried, treated with activated charcoal, filtered and evaporated down to give a brown oil which was distilled under high vacuum to give a colourless oil (22.2 g) bp. 110°–112°/0.02 mmHg.

3C. N-[3-phenylpropenoyl]-3-butyloxyphenethylamine

To a solution of 2-(3-butyloxyphenyl)ethylamine (1.0 g) in acetonitrile (40 cm$^3$) was added powdered potassium carbonate (0.80 g). Cinnamoyl chloride (1.03 g) was then added portionwise over a period of fifteen minutes and the reaction mixture was then stirred at room temperature for 6.5 hours after which distilled water (40 cm$^3$) was added. The mixture was left to stand overnight and was then filtered and extracted several times with ethyl acetate. The combined ethyl acetate extracts were washed successively with potassium bicarbonate solution, water and 0.5M hydrochloric acid before drying over sodium sulphate and then evaporating down to give the product as a tan coloured oil (1.60 g).

3D. 6-Butyloxy-3,4-dihydro-1-styrylisoquinoline hydrochloride

To a solution of the product from Example 3A (5.20 g) in dry, ethanol free chloroform (50 cm$^3$) was added phosphoryl chloride (6.5 cm$^3$). The reaction mixture was heated under reflux for six hours and was then evaporated down to give a brown oil which was treated with water, warmed and stirred well. After allowing to cool, the aqueous phase was decanted off and the residual gummy solid was dissolved in boiling acetone. Addition of acetone and ether, followed by cooling resulted in the title compound crystallising from solution as pale yellow prisms (1.19 g) m.p. 214°–217° C. Analysis: Calculated for: $C_{21}H_{23}NO.HCl$: C, 73.79; H, 7.03; N, 4.10; Found: C, 73.71; H, 7.17; N, 4.28.

3E. 6-Butyloxy-3,4-dihydro-1-styrylisoquinoline hydrogen fumarate

The product from Example 3A was treated with phosphoryl chloride in a manner analogous to that described in Example 3B except that the crude product was treated with 2N sodium hydroxide and ethylacetate. The organic phase was then dried over sodium sulphate and evaporated down to give a clear oil which was dissolved in ether, the solution then being added to a solution of fumaric acid in methanol and ether. The product was obtained as bright green/yellow crystals m.p. 179°–182° C. Analysis: Calculated for: $C_{21}H_{23}NO.C_4H_4O_4$: C, 71.26; H, 6.41; N, 3.33; Found: C, 71.04; H, 6.57; N, 3.16.

3F. 6-Butyloxy-3,4-dihydro-1-styrylisoquinoline perchlorate

The product of Example 3E was dissolved in dilute alkali and the free base was extracted into ether. The ethereal solution was dried, filtered and was then treated with perchloric acid in acetone to give lime yellow crystals. m.p. 228°–230° C. Analysis: Calculated for: $C_{21}H_{23}NO.HClO_4$: C, 62.15; H, 5.92; N, 3.45: Found: C, 62.44; H, 5.98; N, 3.41.

In a similar manner, by treatment of an ethereal solution of the free base with an appropriate acid, the following salts were formed:

nitrate: m.p. 181°–183° C. Analysis, Calculated for: $C_{21}H_{23}NO.HNO_3$: C, 68.48; H, 6.52; N, 7.61: Found: C, 68.20; H, 6.58; N, 7.56.

hydrobromide: m.p. 243°–246° C. Analysis, Calculated for: $C_{21}H_{23}NO.HBr$: C, 65.28; H, 6.22; N, 3.63: Found: C, 65.55; H, 6.27; N, 3.62.

hydrogen sulphate m.p. 205°–206° C. Analysis, Calulcated for: $C_{21}H_{23}NO.H_2SO_4$: C, 62.53; H, 6.20; N, 3.47: Found: C, 62.72; H, 6.21; N, 3.47.

p-toluenesulphonate m.p. 126°–129° C. Analysis, Calculated for: $C_{21}H_{23}NO.C_7H_8SO_3.0.25\ H_2O$: C, 69.78; H, 6.54; N, 2.91: Found: C, 69.70; H, 6.46; N, 2.85.

D-hydrogen tartrate m.p. 158°–160° C. Analysis, Calculated for: $C_{21}H_{23}NO.D(CHOH.CO_2H)_2$: C, 65.93; H, 6.37; N, 3.08; Found: C, 65.77; H, 6.42; N, 3.11.

di-hydrogen phosphate sesquihydrate m.p. 128°–132° C. Analysis, Calculated for: $C_{21}H_{23}NO.H_3PO_4.1.5H_2O$; C, 58.60; H, 6.74; N, 3.26; Found: C, 58.48; H, 6.62; N, 3.22.

EXAMPLE 4

1-(2-Chlorostyryl)-3,4-dihydro-6-propyloxyisoquinoline

4A. N-(2-Chlorocinnamoyl)-3-propyloxyphenethylamine

To a solution of 2-(3-propyloxyphenyl)ethylamine prepared in a manner analogous to that described in Example 1E (2.69 g) in acetonitrile (40 cm³) was added triethylamine (3 cm³). A solution of 2-chlorocinnamoyl chloride (3.6 g) in acetonitrile (20 cm³) was added slowly, the reaction mixture being cooled in an ice bath. When addition was complete, the mixture was stirred at room temperature for 40 minutes, treated with water (60 cm³) and SVM (2 cm³) and stirred well. The resulting precipitate was filtered off, washed and air-dried (5.49 g) m.p. 96°–99° C.

4B. 1-(2-Chlorostyryl)-3,4-dihydro-6-propyloxyisoquinoline hydrochloride

The amide (5.45 g) produced in Example 27A was dissolved in dry, ethanol free chloroform (50 cm³), phosphoryl chloride (6 cm³) was added and the resulting mixture was heated under reflux for a period of four and a half hours. The mixture was then evaporated down and the residual oil was triturated to give a yellow solid which was dissolved in hot SVM (20 cm³). A portion of the solution was treated with ether to cause the title compound to crystallise out as the hydrochloride salt which was filtered off, washed and dried (1.0 g) m.p. 199°–202° C. Analysis; Calculated for $C_{20}H_{20}ClNO.HCl.0.25H_2O$; C, 65.48; H, 5.87; N, 3.82; Found; C, 65.57; H, 5.95; N, 3.80.

The remaining portion (8 cm³) was partitioned between saturated potassium bicarbonate and ether, the ether layer being separated and washed twice more with base before being dried, filtered and then added slowly to a solution of p-toluene sulphonic acid. The resulting precipitate of bright yellow crystals was filtered off, washed and dried (1.70 g) m.p. 145°–147° C. Analysis; Calculated for $C_{20}H_{20}ClNO.C_7H_8SO_3.0.33-H_2O$; C, 64.34; H, 5.69; N, 2.78; $H_2O$ 1.19%; Found; C, 64.38; H, 5.64; N, 2.74; loss at 100° C. was 1.22%.

EXAMPLES 5–94

According to methods analogous to those described in Examples 1–4, the following compounds were prepared. For all compounds listed, satisfactory elemental analyses were obtained, i.e. the analytically obtained elemental compositions were within 0.4% of the calculated values. For each of the listed compounds, nuclear magnetic resonance (n.m.r.) spectra were in accordance with the structures described.

The following abbreviations have been used:
Me=methyl
Et=ethyl
Pr=propyl
But=butyl

| Compound Number | Salt (moles acid if ≠1) | Hydration (moles water) | Melting Point (°C.) |
|---|---|---|---|
| 5 | $HNO_3$ | 0.25 | 159–161 |
| 6 | $HClO_4$ | — | 201–203 |
| 6 | tosylate | 1 | 134–135 |
| 6 | H-tartrate | 2 | 80–80.5 |
| 6 | $H_3PO_4$ (1.6) | — | 78–79 |
| 6 | H-oxalate | — | 147–148 |
| 6 | $HNO_3$ | 0.33 | 153.154 |
| 6 | HBr | 0.5 | 181–183 |
| 7 | HBr | 0.5 | 178–180 |
| 8 | $HNO_3$ | — | 159–162 |
| 9 | H-oxalate (2) | 2 | 139–140 |
| 10 | HCl | 0.33 | 171–173 |
| 10 | H-fumarate | 0.25 | 144–145 |
| 10 | H-tosylate | 1 | 136–138 |
| 10 | H-phthalate | 0.25 | 90–91 |
| 10 | H-succinate | — | 105–106 |
| 10 | HBr | 0.5 | 193–194 |
| 10 | $HClO_4$ | — | 173–174 |
| 10 | $HNO_3$ | — | 151–152 |
| 10 | $H_2SO_4$ | 0.5 | 214–215 |
| 11 | HCl | 1 | 179–181 |
| 12 | HCl | 1.5 | 183–185 |
| 13 | HCl | 0.66 | 218–220 |
| 14 | H-fumarate (1.4) | — | 150–153 |
| 15 | HCl | 4.5 | 226–228 |
| 16 | HCl | 2.5 | 205–207 |
| 17 | HCl | 2 | 219–221 |
| 18 | HCl | 2.25 | 200–202 |
| 19 | HCl | 1 | 210–212 |
| 20 | HCl | 0.5 | 209–211 |
| 21 | HCl | 0.5 | 220–222 |
| 22 | HCl | — | 234–236 |
| 23 | HCl | — | 158–159 |
| 23 | H-oxalate (1.5) | — | 147–148 |
| 24 | HCl | 1 | 194–196 |
| 25 | HCl | 2.5 | 180–183 |
| 26 | HCl | — | 230–233 |
| 27 | HCl | 0.25 | 242–243 |
| 27 | H-fumarate | 0.25 | 154–155 |
| 28 | HCl | — | 234–235 |
| 28 | H-fumarate (1.5) | 1 | 133–135 |
| 29 | HCl | 2 | 180–181 |
| 29 | H-phthalate | — | 118–119 |
| 29 | H-fumarate | 0.25 | 149–150 |

| Compound Number | Salt (moles acid if ≠1) | Hydration (moles water) | Melting Point (°C.) |
| --- | --- | --- | --- |
| 30 | HCl | — | 239–242 |
| 30 | H-oxalate | — | 156–159 |
| 31 | HCl | — | 229–231 |
| 31 | HClO$_4$ | — | 231–232 |
| 32 | HCl | 2 | 206–208 |
| 32 | H-fumarate | 0.5 | 138–139 |
| 33 | HCl | 1 | 218–221 |
| 34 | HCl | 2 | 174–176 |
| 35 | HCl | 0.5 | 228–230 |
| 36 | HCl | 0.33 | 233–235 |
| 37 | HCl | 0.5 | 228–230 |
| 38 | HCl | 0.25 | 232–234 |
| 39 | HNO$_3$ | — | 146–148 |
| 40 | HCl | — | 224–226 |
| 41 | tosylate | 0.25 | 180–181 |
| 42 | HCl | 0.5 | 194–196 |
| 43 | HCl | 2.5 | 142–145 |
| 44 | HCl | 0.33 | 149–152 |
| 45 | HCl | 0.25 | 218–220 |
| 46 | HCl | — | 223–225 |
| 47 | HCl | 0.5 | 197–199 |
| 48 | HCl | — | 231–234 |
| 49 | HCl | 0.25 | 225–227 |
| 50 | HCl | 1.5 | 214–216 |
| 51 | HCl | — | 243–244 |
| 52 | HCl | 2.5 | 198–199 |
| 52 | H-phthalate | — | 149–150 |
| 52 | tosylate | 1 | 234–235 |
| 52 | mesylate | 0.33 | 211–212 |
| 52 | H-oxalate | 0.25 | 195–197 |
| 52 | H-tartrate | — | 160–161 |
| 52 | H-fumarate | — | 159–160 |
| 52 | HClO$_4$ | — | 206–207 |
| 52 | HNO$_3$ | — | 143–145 |
| 52 | H$_3$PO$_4$ | 2 | 210–211 |
| 53 | HCl | 1 | 210–211 |
| 54 | HCl | 0.66 | 198–200 |
| 55 | HCl | 2.5 | 192–195 |
| 56 | H-fumarate | 0.75 | 173–175 |
| 57 | HCl | — | 207–209 |
| 57 | H-tartrate | — | 165–166 |
| 58 | HCl | 2.25 | 194–196 |
| 59 | HCl | 2.5 | 201–204 |
| 60 | H-fumarate | 0.25 | 172–174 |
| 61 | HCl | 1 | 203–204.5 |
| 62 | HCl | 1 mole MeOH | 196–198 |
| 63 | HCl | — | 215–217 |
| 64 | HBr | — | 196–198 |
| 64 | tosylate | 0.5 | 172–173 |
| 64 | HNO$_3$ | — | 133–134 |
| 65 | HCl | 1.5 | 172–175 |
| 66 | H-oxalate | — | 152–154 |
| 67 | HCl | 0.25 | 193–197 |
| 68 | HCl | 1 | 186–189 |
| 69 | H-oxalate | — | 128–130 |
| 70 | (D)-H-tartrate | 1.5 | 117–119 |
| 71 | HCl | — | 215–217 |
| 72 | HCl | 0.75 | 225–226 |
| 73 | HCl | 1.25 | 216–218 |
| 74 | HCl | 0.5 | 186–188 |
| 74 | H-fumarate | 0.25 | 135–136 |
| 75 | HCl | — | 212–214 |
| 75 | tosylate | — | 170–173 |
| 76 | HCl | 1.25 | 175–177 |
| 76 | H-oxalate | 1 | 124–127 |
| 77 | HCl | — | 209–211 |
| 78 | HCl | — | 212–214 |
| 79 | HCl | 0.25 | 194–196 |
| 80 | H$_2$SO$_4$ | 0.25 | 193–195 |
| 81 | HNO$_3$ | 0.5 | 147–149 |
| 82 | HCl (2) | 1.0 | 190–191 |
| 83 | HCl | — | 219–220 |
| 84 | HCl | 0.33 | 210–212 |
| 85 | HCl | 1.5 | 206–207 |
| 86 | HCl | 1.3 | 175–178 |
| 87 | HCl | 1 | 187–189 |
| 88 | HCl | 0.5 | 212–214 |
| 89 | HCl | 2 | 192–194 |
| 90 | HCl | 0.5 | 195–197 |
| 91 | HCl | 0.5 | 187–189 |
| 92 | HCl | — | 215–217 |
| 93 | HCl | 1.25 | 205–207 |
| 94 | H-fumarate | — | 162–164 |
| 95 | H-fumarate | — | 160–161 |
| 95 | HBr | 0.75 | 88–90 |
| 96 | H-fumarate | — | 174–175 |
| 97 | HCl | — | 205–206 |
| 98 | HCl | — | 212–214 |
| 99 | HCl | 1 | 212–214 |
| 100 | HCl | — | 189–191 |
| 101 | HCl | 0.25 | 187–189 |

EXAMPLE 102

(E)-6-Butyloxy-3,4-dihydro-1-[2-(4-bromo-2-thienyl)-vinyl]isoquinoline hydrochloride 102A. (E)-4-Bromo-3-(2-thienyl)acrylic acid Malonic acid (16.2 g) was added to a solution of 4-bromothiophen-2-aldehyde (25.1 g) in pyridine (100 cm$^3$) and piperidine (3.2 cm$^3$) and the resulting mixture was heated at 100° C. for 6.5 hours, allowed to cool to room temperature overnight and was then evaporated down to give a beige semi-solid. The semi-solid was treated with aqueous potassium hydroxide solution and the resulting mixture was diluted with water (50 cm$^3$), acidified with concentrated hydrochloric acid (90 cm$^3$) and then cooled to yield a precipitate which was filtered off, washed with ether/40–60 petrol and was then sucked dry (26.1 g) m.p. 167°–169° C. (aqueous methanol) Analysis; Calculated; C, 36.05; H, 2.15; Found; C, 36.30; H, 2.03.

102B. N-[3-(3-Bromo-2-thienyl)prop-2-enoyl]-m-butyloxyphenethylamine

The product from Example 102A (1 g) was dissolved in dry benzene (5 cm$^3$) and heated at reflux in the presence of thionyl chloride (2 cm$^3$) for 4.5 hours before evaporating down to give the acid chloride as a fawn crystalline solid (1.07 g) m.p. 89°–91° C.

Powdered potassium carbonate (1.7 g) was added to a solution of 2-(3-butyloxy phenyl)ethylamine (2.1 g) (prepared by the method Example 1) in acetonitrile (30 cm$^3$) and the acid chloride (3.24 g), prepared as described above, in acetonitrile (30 cm$^3$) was added dropwise over ten minutes. The reaction mixture was stirred at room temperature for 4 hours, treated with water (60 cm$^3$) and then extracted with ether (3×60 cm$^3$). The combined ether extracts were washed successively with 1M sodium hydroxide solution, water and 1M hydrochloric acid and were then dried over sodium sulphate, filtered and evaporated to give the title compound as a pale tan mobile oil (4.83 g).

102C. (E)-6-Butyloxy-3,4-dihydro-1-[2-(4-bromo-2-thienyl)vinyl]isoquinoline hydrochloride The product from 102B (4.4 g) was dissolved in dry ethanol-free chloroform and was treated with phosphoryl chloride (5 cm$^3$) in a manner analogous to that described in Example 3. After recrystallisation from a mixture of ether, methanol and acetone, the product was obtained as yellow needles (2.76 g) m.p. 196°–198° C. Analysis; Calculated for C$_{19}$H$_{20}$Br NOS.HCl; C, 53.46; H, 4.92; N, 3.28; Found; C, 53.34; H, 4.94; N, 3.04.

EXAMPLE 103

6-Butyloxy-3,4-dihydro-1-[2-(5-bromo-2-thienyl)vinyl]isoquinoline hydrochloride

96A. N-[3-(2-Bromo-2-thienyl)prop-2-enoyl]-m-butyloxyphenethylamine

Malonic acid (6.47 g) was reacted with 5-bromothiophen-2-aldehyde (10 g) according to the method of Example 102A to give 3-[2-(5-bromothienyl)]prop-2-enoic acid (9.16 g) m.p. 207°–209° C. which was then converted to the acid chloride (m.p. 169°–171° C.) according to the method described in Example 102B.

The acid chloride was then used to acylate 2-(3-butyloxyphenyl)ethylamine by the method described in Example 102B affording the product as a dark tan oil. 103B.6-Butyloxy-3,4-dihydro-1-[2-(5-bromo-2-thienyl)-vinyl]isoquinoline The amide (4.6 g) prepared in Example 103A was cyclised according to the procedure of Example 102C to give the title compound (2.89 g) as bright yellow needles which were recrystallised from a mixture of acetone, methanol and ether m.p. 228°–230° C. Analysis; Calculated for $C_{19}H_{20}BrNOS \cdot HCl \cdot 0.66H_2O$; C, 51.99; H, 4.94; N, 3.19; Found; C, 52.03; H, 4.82; N, 2.86.

EXAMPLES 104–146

The following compounds were made according to methods analogous to those described in Examples 102 and 103.

| Compound Number | Salt (moles as if ≠1) | Hydration (moles water) | Melting Point (°C.) |
|---|---|---|---|
| 104 | HCl | 0.5 | 195–196 |
| 104 | HNO3 | — | 170–172 |
| 105 | HCl | — | 211–213 |
| 106 | HCl | 0.75 | 205–206 |
| 107 | HCl | — | 216–219 |
| 108 | HCl | — | 198–200 |
| 109 | HCl | 1 | 199–201 |
| 109 | HNO3 | — | 181–183 |
| 110 | H-fumarate | 0.25 | 150–151 |
| 110 | HBr | — | 224–225 |
| 111 | HBr | — | 212–213 |
| 112 | tosylate | — | 174–175 |
| 112 | H-fumarate | 0.5 | 161–162 |
| 112 | H-phthalate | — | 143–144 |
| 113 | HCl | — | >350 |
| 114 | HCl | 0.75 | 205–207 |
| 115 | HCl | 0.5 | 213–215 |
| 116 | HNO3 | — | 161–163 |
| 117 | HNO3 | — | 195–196 |
| 118 | HNO3 | — | 179–180 |
| 119 | HNO3 | 0.25 | 187–189 |
| 119 | H-fumarate | — | 142–144 |
| 120 | H2SO4 | — | 180–182 |
| 121 | H-fumarate | 1 | 166–168 |
| 121 | HNO3 | — | 181–183 |
| 122 | tosylate | — | 182–184 |
| 122 | H2SO4 | — | 235–237 |
| 123 | HCl | 1.75 | 180–183 |
| 123 | H2SO4 | 0.66 | 200–202 |
| 124 | HCl(2) | — | 220–222 |
| 124 | HNO3(2) | — | 165–167.5 |
| 125 | HNO3(2) | — | 157–158 |
| 126 | H-fumarate | 0.25 | 152–153 |
| 126 | HCl | 125 | 182–183 |
| 127 | HNO3 | — | 152–153 |
| 127 | HBr | — | 194–195 |
| 128 | HNO3 | — | 139–141 |
| 129 | HNO3 | — | 138–139 |
| 130 | HNO3 | — | 133–136 |
| 131 | HCl | 1 | 239–241 |
| 132 | HCl | — | 217–219 |
| 132 | HBr | — | 242–243 |
| 133 | HCl | 0.33 | 223–224 |
| 133 | H-fumarate | 1.25 | 183–185 |
| 134 | HCl | 0.33 | 215–217 |
| 134 | tosylate | — | 176–177 |
| 135 | HCl | 1.5 | 214–216 |
| 135 | HCl | 0.25 | 174–175 |
| 136 | HCl | 0.25 | 211–212 |
| 136 | H-phthalate | — | 158–159 |
| 137 | HNO3 | 0.25 | 125–126 |
| 138 | HNO3 | 0.25 | 141–142 |
| 139 | HNO3 | — | 139–141 |
| 140 | HNO3 | — | 180–181 |
| 140 | H-fumarate | 1 | 165–166 |
| 141 | HCl | 1.5 | 112–114 |
| 142 | HNO3 | — | 183–184 |
| 143 | HCl | 1.25 | 209–214 |
| 144 | HNO3 | — | 199–201 |
| 145 | HNO3 | — | 210–212 |
| 146 | HCl | 1 | 198–200 |
| 146 | HNO3 | — | 188–190 |
| 202 | HCl(2) | 2 | 191–193 |
| 203 | HCl(2) | 1 | 149–151 |

EXAMPLE 147

(Z)-1-(1-Bromo-2-phenylvinyl)-6-butyloxy-3,4-dihydroisoquinoline 147A. 2-(3-Butyloxyphenyl)ethylamine Raney nickel catalyst (approx 5 g) was added to a solution of 3-butyloxybenzyl cyanide (38.64 g, prepared according to example 1 D) in saturated ammoniacal methanol (700 cm$^3$). The resulting mixture was heated at 70° C. in the presence of hydrogen (45 Atmospheres) for two hours and was then allowed to cool to room temperature overnight. The cooled mixture was filtered to remove the catalyst and was then evaporated down to give a green oil (42.2 g).

147B. N-(2-Bromo-3-phenylacryloyl)-2-(3-butyloxyphenyl)ethylamine

A mixture of α-bromocinnamic acid (6.81 g), dry chloroform (50 cm$^3$) and thionyl chloride (5 cm$^3$) was heated under reflux for 5.5 hours by which time evolution of HCl had ceased. The pale yellow solution was then evaporated to dryness to give the acid chloride as a pale yellow oil (7.35 g).

A portion of the acid chloride (3.6 g) was dissolved in acetonitrile (10 cm$^3$) and was added to a mixture of 2-(3-butyloxyphenyl)ethylamine (2.9 g) and powdered potassium carbonate (3 g) in acetonitrile (30 cm$^3$). The resulting mixture was stirred at room temperature for one hour before partitioning between water and ether (50 cm$^3$). The organic phase was washed with water followed by 0.5M hydrochloric acid, was dried over sodium sulphate, filtered and evaporated to give a pale tan oil which solidified to give cream waxy needles (5.00 g) mp=38°–39° C.

147C. (Z)-1-(1-Bromo-2-phenylvinyl)-6-butyloxy-3,4-dihydroisoquinoline hydrogen oxalate The product of example 147B (4.9 g) was treated with phosphoryl chloride (6 cm$^3$) in dry ethanol-free chloroform according to the method described in Example 1G to give, after work-up and treatment with oxalic acid, the title compound as a cream crystalline solid (2.00 g) mp 159°–160°. Analysis. Calculated for $C_{21}H_{22}BrNO \cdot C_2H_2O_4$, C, 58.22; H, 5.06; N, 2.95. Found; C, 58.36; H, 5.09; N, 2.9).

T.l.c. (Silica gel), solvent methanol: chloroform (1:4), one spot R$_f$ 0.77.

EXAMPLES 148–154

According to the method described in Example 147, the compounds listed below were prepared:

| Compound Number | Salt (moles acid if = 1) | Hydration (moles water) | Melting Point (°C.) |
|---|---|---|---|
| 148 | H-oxalate | 0.25 | 159–160 |
| 149 | H-oxalate | 1 | 166–168 |
| 149 | H₂SO₄ | — | 168–170 |
| 150 | HNO₃ | 1 | 109–111 |
| 151 | HNO₃ | — | 135–137 |
| 151 | H-oxalate | — | 160–162 |
| 152 | HBr | 0.33 | 186–188 |
| 152 | H₂SO₄ | — | 180–184 |
| 153 | H-oxalate | — | 175–176 |
| 154 | HNO₃ | 0.25 | 154–155 |

EXAMPLE 155

1-(2,4-Dichlorostyryl)-3,4-dihydro-6,7-dipropyloxy isoquinoline 155A. 3,4-Dipropyloxy benzaldehyde A 50% suspension of sodium hydride (15.9) in mineral oil was washed with sodium dried ether (2×50 cm³) under nitrogen before the addition of dimethylformamide (300 cm³). The mixture was cooled and 3,4-dihydroxybenzaldehyde (20.7 g) was then added slowly. After a 15 minute stirring period propyliodide (56.1 g) was added dropwise over 10 minutes and the resulting mixture was stirred at room temperature for 4 hours before allowing to stand overnight. The mixture was then poured into water and extracted with ether (200 cm³ followed by 3×150 cm³). The combined ether extracts were washed with 2N sodium hydroxide (2×100 cm⁵) followed by water (2×100 cm³) and the washings were further extracted with ether (2×100 cm³). After drying over sodium carbonate, the ether phase was treated with activated charcoal, and was then filtered and evaporated down to give a dark brown oil (16.7 g) bp/0.05 mm Hg 110°–115° C. $V_{max}$ 1690, 1510, 1270, 1135.

155B. 1-(3,4-Di-propyloxyphenyl)-2-nitroethene

The product of Example 155A (4.44 g) was reacted with nitromethane under conditions analogous to those described in Example 3A to afford the title compound as a yellow crystalline solid (3.3 g) mp=109°–112° C. ¹H NMR (CDCl₃) 0.8–1.2 (6H, t) 1.5–2.1 (4H, sextet) 3.8–4.1 (4H, triplet of doublets), 6.7–7.2 (3H, m) 7.34′1H, d (J=13 Hz)) 7.84 (1H, d(J=13 Hz)).

155C. 2-(3,4-Di-propyloxyphenyl)ethylamine

The product of Example 155B (10.5 g) was reduced with lithium aluminum hydride according to the procedure of Example 3B to give the title compound as a tan coloured oil (8.8 g) bp/0.05 mm=114°–116° C. IR max (cm⁻¹) 3380, 1515, 1265.

155D. N-[2,4-dichlorocinnamoyl]-2-[3,4-dipropyloxyphenyl]ethylamine

The product of Example 155C (2.4 g) was acylated with 2,4-dichlorocinnamoyl chloride in acetone solution in the presence of potassium carbonate in a manner similar to that described in Example 1F. The title compound was obtained as a light yellow crystalline solid. (4.5 g) mp=132°–134° C. (methanol).

155E. 1-(2,4-Dichlorostyryl)-3,4-dihydro-6,7-dipropyloxy isoquinoline hydrochloride The product of Example 155D (2.6 g) was treated with phosphoryl chloride (1.9 g) according to the method of Example 1G. Following work-up and recrystallisation from acetone/ether, the title compound was obtained as fine yellow needles (2.0 g) mp 171°–173° C. Analysis calculated for C₂₃H₂₅Cl₂NO₂.HCl.2H₂O, C, 56.26; H 6.11; N, 2.85; H₂O 7.34 Found; C, 55.94; H, 5.72; N, 2.83; loss at 105° C.; 7.43%.

T.l.c. (silica gel) n-butanol: water: ethyl acetate: acetic acid (1:1:1:1), one spot $R_f$ 0.74.

IR $V_{max}$ (cm⁻¹) 1595, 1580, 1370, 1335, 1275.

monohydrate mp 179°–181° C.

The free base was obtained by basifying an aqueous solution of the hydrochloride salt with potassium bicarbonate and extracting with ether. Drying of the ether layer, evaporation of the solvent and crystallisation of the residue from pentane/ether gave pale cream needles. mp 93.5°–94.0° C. Analysis calculated for C₂₃H₂₅Cl₂NO₂; C, 66.08; H, 5.99; N, 3.35 Found; C, 66.46; H, 6.02; N, 3.14.

EXAMPLE 156

1-(4-Chlorostyryl)-3,4-dihydro-3-methyl-6,7-dipropyloxyisoquinoline 156A. 1-(3,4-Dipropyloxyphenyl-2-nitroprop-1-ene A mixture of 3,4-di-n-propylbenzaldehyde (22.2 g, obtained according to Example 155A), nitroethane (9.7 g), n-butylamine (2.5 cm³) and toluene (50 cm³) was heated under reflux in a Dean-Stark apparatus for three days by which time the theoretical amount of water had been azeotropically removed. The mixture was then evaporated down to give a brown oil. The oil was then treated with water (15 cm³), cooled to 0°–3° C. and methanol added until crystallisation occurred. The dark golden solid was filtered off and sucked dry (21.0 g) mp=49°–52° C.

156B. 2-Amino-1-(3,4-dipropyloxyphenyl)propane

The product of Example 156A was reduced with lithium aluminum hydride according to the method of Example 155B. Work-up and distillation under high vacuum gave a colourless oil (22.4 g) bp/0.05 mm Hg 124°–130° C.

156C. N-[4-Chlorocinnamoyl]-3-[3,4-dipropylphenyl]-prop-2-ylamine

The product of 156B (4.0 g), triethylamine (3.6 g), and potassium carbonate (4.8 g) in dry ethanol free chloroform (45 cm³) were stirred together at room temperature for 30 minutes and then 4-chlorocinnamoyl chloride (3.6 g) was added portionwise, care being taken to ensure that the temperature remained between 15° and 20° C. The resulting mixture was then stirred at room temperature for 6 hours before extracting successively with water (45 cm³), 2M HCl(45 cm³), 2M NaOH (45 cm³) and finally water (45 cm³).

The organic phase was dried over anhydrous sodium carbonate, treated with hyflo/charcoal, filtered and evaporated to give a pale yellow solid (6.55 g) which was recrystallised from methanol to give an off-white solid (3.1 g) mp 142°–144° C.

156D. 1-(4-Chlorostyryl)-3,4-dihydro-3-methyl-6,7-dipropyloxyisoquinoline

A solution of the product of Example 156C (3.1 g) in dry ethanol free chloroform was treated with phosphoryl chloride according to the method of Example 1G. Following work-up and crystallisation from ethanol: ether: petrol (1:5:4) the product was obtained as yellow needles (1.7 g) mp 117°–119° C.

T.l.c. (Silica gel, n-BUOH: H₂O: H Ac: EtOAc (1:1:1:1), one spot $R_f$=0.72. T.l.c. (Silica gel, MeOH: CHCl₃ (1:4). one spot $R_f$=0.69.

Dihydrate mp 109°–111° C. Analysis Calculated for $C_{24}H_{28}ClNO_2$, HCl 2$H_2O$, C, 61.27; H, 7.02; N, 2.98; $H_2O$, 7.66. Found; C, 61.09; H, 6.79; N, 2.78; loss at 100° C.=7.68%.

EXAMPLES 157–183

By methods analogous to those described in Examples 141 and 142, the following compounds were prepared.

| Compound Number | Salt (moles acid if ≠ 1) | Hydration (moles water) | Melting Point (°C.) |
| --- | --- | --- | --- |
| 157 | HCl | 1 | 108–111 |
| 158 | HCl | 1 | 182–184 |
| 159 | HCl | 3 | 111–113 |
| 160 | HCl | 1 | 130–132 |
| 161 | HCl | 0.75 | 175–176 |
| 162 | HCl | 0.25 | 209–210 |
| 163 | HCl | 1.75 | 84–86 |
| 164 | HCl | 1 | 98–101 |
| 165 | HCl | 2.5 | 108–110 |
| 166 | H-oxalate | 0.25 | 192–193 |
| 167 | HCl | 3 | 162–165 |
| 168 | HCl | 1 | 167–168 |
| 169 | HCl | 0.5 | 142–144 |
| 170 | $H_2SO_4$ | 1 | 179–181 |
| 171 | HCl | 0.3 | 193–195 |
| 172 | HCl | 0.75 | 209–210 |
| 173 | HCl | 1.25 | 196–198 |
| 174 | H-tartrate | 1 | 149–153 |
| 175 | HCl | 2.5 | 205–206 |
| 176 | HCl | 2 | 155–156 |
| 177 | H-oxalate (1.4) | — | 142–144 |
| 178 | HCl | 1.5 | 135–138 |
| 179 | HCl | 0.75 | 140–143 |
| 180 | HCl | 1 | 218–220 |
| 181 | HBr | — | 226–228 |
| 182 | HCl | 2.5 | 180–183 |
| 183 | H-oxalate | 0.5 | 137–139 |

EXAMPLE 184

1.2.3.4-Tetrahydro-6,7-dibutyloxy-1-(4-chlorostyryl-)isoquinoline hydrochloride hemihydrate The product of Example 157 (1.0 g) in a water: methanol (1:1) mixture (80 cm³) at 0° C. was treated with sodium borohydride (0.1 g) over a period of ten minutes. After stirring at room temperature for ninety minutes, benzene (50 cm³) was added and the resulting mixture was extracted with ether (2×100 cm³). The combined organic layers were washed with brine (2×50 cm³), dried over sodium sulphate, filtered and were then evaporated to dryness to give a cream coloured solid (0.85 g). The solid was dissolved in ether (25 cm³) and the title compound was precipitated from solution by the addition of ethereal hydrogen chloride (2 cm³). Yield=0.76 g mp 189°–190° C. Analysis Calculated for $C_{25}H_{32}$ Cl $NO_2.HCl.0.5H_2O$; C,65.35; H,7.40; N,3.05 Found; C,65.50; H, 7.51; N,3.07.

EXAMPLE 185

1-(4-Chlorostyryl)-1,2,3,4-tetrahydro-6,7-dipropyloxyisoquinoline hydrochloride

By the method of Example 184, the product of Example 168 was reduced with sodium borohydride to give the title compound as colourless needles. mp 229°–231° C. Analysis Calculated for $C_{23}$ $H_{28}$ Cl $NO_2.HCl$; C,65.40; H,6.87; N,3.32 Found; C,65.11; H,6.94; N,3.22.

EXAMPLE 186

186A. Ethyl(3-propyloxy phenyl)acetate

A mixture of ethanol (3.9 g), water (0.2 g), conc.sulphuric acid (3.9 g) and 3-propyloxyphenylacetonitrile (3.5 g; 20 mmol) was heated under reflux during 6 hours. After cooling, ether (20 ml) and water (20 ml) were added and the mixture was stirred. The phases were separated and the ethereal extract washed with 10% potassium bicarbonate (2×20 ml), dried over $Na_2SO_4$, filtered and evaporated to dryness to give a pale tan oil.
Y=4.03 g (90.8%).

186B. 2-Methyl-3-(3-propyloxyphenyl)propan-2-ol

A solution of methyl magnesium iodide in dry ether (100 ml) was prepared from magnesium (1.9 g; 77.3 mmol) and iodomethane (11.0 g; 77.5 mmol) using standard procedure. A solution of ethyl (3-propyloxyphenyl)acetate (7.8 g; 35 mmol) in ether (20 ml) was added over 10 minutes to the methyl magnesium iodide. After stirring for 30 mins at 25°, the mixture was heated under reflux during 2 hours, cooled to −5°, treated cautiously with saturated ammonium chloride solution (50 mls) followed by conc. HCl (25 ml). The phases were separated and the organic layer washed with 10% brine (2×20 ml), dried over $Na_2SO_4$, filtered and evaporated to dryness to give a pale tan oil.
Y=7.1 g (97.2%).

186C. 3,4-Dihydro-3,3-dimethyl-6-propyloxy-1-styryl isoquinoline hydrogen oxalate, 1.25 hydrate To a solution of 2-methyl-3-(3-propyloxy)propan-2-ol (1.02 g; 5.0 mmol) in trifluoroacetic acid (8 ml) at 20° was added trifluoroacetic anhydride (0.94 g; 5.5 mmol) followed by cinnamoyl nitrile (0.72 g; 5.0 mmol). The temperature of the reaction mixture rose rapidly to 40° C. The reaction mixture was then stirred at 25°–28° C. for 2 hours, poured onto ice/water (75 g), basified (pH 9–9.5) with 10M NaOH and the liberated basic material extracted into ether (3×20 ml). The combined extracts were washed with 20% brine (2×20 ml), dried over $Na_2SO_4$, filtered and the filtrate introduced into a stirred solution of oxalic acid (0.5 g) in warm acetone (10 ml). On standing, yellow prisms were deposited
Y=1.85 g (90.3%).
mpt 175°–176° (effervesc).
Anal. Found C, 66.66; H, 6.60; N, 2.98%, Req C, 66.74; H, 6.83; N, 3.24%.
Tlc (silica gel), solvent $BuOH:H_2O:EtOAc:HOAc$ (1:1:1:1), one spot Rf 0.80 $CHCl_3$-MeOH (4:1), one spot Rf 0.60.

EXAMPLE 187

187A. 2-Methyl-2-(3-propyloxyphenyl)propionitrile

To a suspension of sodium hydride (0.5 g; 21 mmol) in dry diglyme (20 ml) was added 3-propyloxyphenyl acetonitrile 1.75 g; 10 mmol) followed by iodomethane (3.12 g; 22 mmol) which was added dropwise over 10 minutes. When the addition was complete, the reaction mixture was stirred at 20° for 2 hours and then poured onto ice/water (100 g). The precipitated oil was extracted into ether (3×20 ml) and the combined extracts dried over $Na_2SO_4$, filtered and evaporated to dryness to give a tan oil which was distilled under reduced pressure to give a colourless oil.
Y=1.96 g (96.5%), bp 116°–118°/0.08 mm Hg.

187B. Ethyl-2-methyl-2-(3-propyloxyphenyl)propionate

The title compound was prepared from 2-methyl-2-(3-propyloxyphenyl)propionitrile using a procedure similar to that described in Example 186A and obtained as a very pale oil in 84.8% yield.

187C. 2,3-Dimethyl-3-(3-propyloxyphenyl)butan-2-ol

The title compound was prepared from ethyl-2-methyl-2-(3-propyloxyphenyl)propionate using a procedure similar to that described for 186B above and obtained as a colourless oil in (95.6%) yield.

187D. 3,4-Dihydro-3,3,4,4-tetramethyl-6-propyloxy-1-styryl isoquinoline hydrogen fumarate, one quarter hydrate The title compound was prepared from 2,3-dimethyl-3-(3-propyloxyphenyl)butan-2-ol (7) using a procedure similar to that described for 186C. The hydrogen fumarate was obtained as bright yellow prisms by adding an ethereal solution of the base to a solution of fumaric acid in hot methanol and cooling.

Y = 1.40 g (39.8%).
mpt 218°–220°.
Anal. Found C,71.87; H, 7.09; N, 3.00%, Req. C,71.87; H, 7.16; N, 2.99%.
Tlc (silica gel), solvent EtOAc-MeOH (4:1), one spot Rf 0.56.

EXAMPLES 188–189

The following compounds were prepared in a manner analogous to that described in Example 186.

188. 6-Butyloxy-3,4-dihydro-3,3-dimethyl-1-styrylisoquinoline hydrogen fumarate, mp 189°–191° C.

189. 3,4-Dihydro-3,3-dimethyl-6-heptyloxy-1-styrylisoquinoline hydrogen fumarate, mp 136°–138° C.

EXAMPLE 190

190A. 1-Amino-2-methyl-2-(3-propyloxyphenyl)propane (3)

To a suspension of $LiAlH_4$ (1.0 g) in dry THF (25 ml) under dry $N_2$ was added a solution of 2-methyl-2-(3-propyloxyphenyl)propionitrile (1.02 g) in dry THF (10 ml) over 10 minutes. After stirring at 25° for 20 minutes, the reaction mixture was heated under reflux for 5 hours, cooled to 0°, diluted with ether (50 ml) and cautiously decomposed with ethyl acetate (2 ml) followed by 5M NaOH (5 ml). The mixture was filtered and the residue triturated with ether (3×10 ml). The combined filtrates were extracted with 20% HCl (4×10 ml) and the combined extracts basified with 10M NaOH. The liberated oil was extracted into ether (3×15 ml) and the combined extracts dried over $Na_2SO_4$, filtered and evaporated to dryness to give a colourless oil.

Y = 0.93 g (89.4%).

190B. N-(Cinnamoyl-2-methyl-2-(3-propyloxyphenyl)-propylamine

A solution of 1-amino-2-methyl-2-(3-propyloxyphenyl)propane (2.07 g; 10 mmol) in acetonitrile was treated with cinnamoyl chloride (1.87 g; 11 mmol) according to the method described in Example 3C to give, after work up, the product as long colourless silky needles (2.72 g, 81%). mp = 86°–88° C.

Anal. Found C; 78.26, H; 7.88, N; 4.06%, Required C; 78.34, H; 8.01, N; 4.15%.

190C. 3,4 Dihydro-4,4-dimethyl-6-propyloxy-1-styrylisoquinoline 1.5 hydrogen fumarate The product of Example 188B was reacted with phosphoryl chloride to give the title compound under conditions analogous to these described in Example 2B Yield = 43.6% mp = 156°–158° C.

Anal. Found C; 68.08, H; 6.10, N; 2.90%, Required C; 68.15, H; 6.28, N; 2.84%.

T.l.c. (silica) $CHCl_3$-MeOH (4:1), one spot Rf 0.58.

EXAMPLE 191

4-Butyloxystyryl-3,4-dihydroisoquinoline

A solution of 1-(2-(2-acetamidoethyl)phenyl)-3-(4-butyloxyphenyl)propenone (3.06 g, 8.38 mmols) in glacial acetic acid (5 cm$^3$) and concentrated hydrochloric acid (30 cm$^3$) was heated under reflux for a period of 3 hours. On cooling, a solid precipitated out. The crude hydrochloride was filtered off and washed with ether. The solid was recrystallised from acetone and ether to give bright yellow coloured prisms, which were filtered off, washed and sucked dry. Yield = 1.69 g (59.1%)M.pt = 83°–87°.

Analysis: Calc: C, 72.83; H, 7.08; N, 4.05%, Found: C, 72.87; H, 7.29; N, 4.00%.

BIOLOGICAL ACTIVITY

EXAMPLE 192

Activity against Trichomonas vaginalis-$IC_{50}$ Determination

Modified Diamonds Medium (MDM) was prepared according to the method described in J. Kulda et al., *American Journal of Obstetrics and Gynaecology* 1970, 108, 908–18 and 4 cm$^3$ of the medium was pipetted into each of a series of tubes (usually 16 tubes). To each tube was added 0.5 cm$^3$ of varying concentration of a solution (usually in ethanol+MDM) or suspension of the test drug. Duplicate tubes for each drug concentration were prepared.

Finally, to each tube was added *T. vaginalis* (0.5 cm$^3$) at a concentration of $1 \times 10^5$ cm$^{-3}$,) to give a final trichomonad concentration of $1 \times 10^4$ cm$^{-3}$ in each tube. The tubes were then incubated (aerobically) at 37° C. and the resulting trichomonad numbers were counted at 24 and 48 hours using a haemacytometer. The average count for each drug level was determined and compared with the untreated controls (which had received 0.5 cm$^3$ control in place of drug concentrate), and from these results the % inhibitions were determined for each drug level.

This information was then used to determine the 50% inhibition concentration ($IC_{50}$). The results are shown in Table 9.

TABLE 9

| | In vitro activity against *T. vaginalis* | | | |
|---|---|---|---|---|
| Compound of Ex. No. | $IC_{50}$ (µg/cm$^3$) 24 hr | 48 hr | Compound of Ex. No. | $IC_{50}$ (µg/cm$^3$) 24 hr | 48 hr. |
| 1 | 1.3 | 1.8 | 113 | 0.7 | 1.2 |
| 2 | 1.0 | 1.8 | 115 | 0.4 | 1.0 |
| 3 | 3.7 | 8.8 | | | |
| 5 | 6.1 | 6.4 | 135 | 1.3 | 1.6 |
| 12 | 1.2 | 2.0 | 104 | 7.4 | 7.3 |
| 13 | 1.5 | 2.5 | 105 | 2.0 | 6.7 |
| 14 | 5.5 | 8.0 | 106 | 1.4 | 3.7 |
| 15 | 1.5 | 2.8 | 108 | 2.7 | 6.1 |
| 19 | 10.0 | 13.5 | 130 | 3.6 | 5.4 |
| 23 | 1.1 | 2.3 | 129 | 2.9 | 3.1 |
| 24 | 1.2 | 128 | 128 | 1.5 | 1.6 |
| 33 | 0.7 | 1.0 | 126 | 1.5 | 1.7 |
| 45 | 2.2 | 2.8 | 137 | 1.0 | 1.7 |
| 46 | 1.1 | 1.3 | 147 | 0.2 | 0.3 |
| 47 | 1.1 | 1.7 | 150 | 0.2 | 0.2 |
| 74 | 3.3 | 0.9 | 151 | 0.3 | 0.3 |
| 75 | 0.3 | 0.8 | 153 | 0.3 | 0.5 |
| 52 | 2.9 | 3.2 | 155 | 1.2 | 2.2 |
| 53 | 3.2 | 5.5 | 157 | 1.8 | 2.1 |
| 56 | 8.0 | 8.0 | 158 | 0.8 | 1.1 |
| 60 | 5.6 | 10.5 | 160 | 0.6 | 1.0 |
| 65 | 1.2 | 1.6 | 161 | 0.7 | 1.4 |
| 68 | 5.0 | 5.3 | 165 | 9.0 | 10.0 |

TABLE 9-continued

| In vitro activity against *T. vaginalis* | | | | | |
|---|---|---|---|---|---|
| Compound of Ex. No. | $IC_{50}$ ($\mu g/cm^3$) 24 hr | 48 hr | Compound of Ex. No. | $IC_{50}$ 24 hr | ($\mu g/cm^3$) 48 hr. |
| 71 | 0.8 | 1.4 | 170 | 1.0 | 3.2 |
| 73 | 0.4 | 1.1 | 171 | 0.8 | 1.8 |
| 80 | 2.5 | 2.4 | 172 | 0.7 | 2.0 |
| 81 | 1.1 | 1.6 | 174 | 1.4 | 2.0 |
| 82 | 0.6 | 2.0 | 175 | 0.4 | 1.0 |
| 85 | 1.1 | 1.5 | 176 | 1.7 | 3.1 |
| 92 | 0.5 | 1.0 | | | |
| 6 | 0.4 | 0.4 | 180 | 1.0 | 1.6 |

FORMULATION EXAMPLES

Example 193 2% Gel

| | % w/w |
|---|---|
| Compound | 2.00 |
| Hydroxypropyl Methyl cellulose (Methocel F4M) | 2.50 |
| Polyox WSR - 205 | 0.25 |
| Propylene glycol | 10.00 |
| Methylparaben | 0.15 |
| Propylparaben | 0.05 |
| Purified Water to | 100.00 |

Example 194 2% Cream

| | % w/w |
|---|---|
| Compound | 2.0 |
| Fractionated Coconut oil (Miglyol 812) | 11.0 |
| Dynaston 114 | 8.0 |
| Tween 60 | 2.3 |
| Tween 80 | 1.2 |
| Propylene glycol | 10.0 |
| Phenylethyl alcohol | 1.0 |
| Purified Water to | 100.0 |

Example 195 Tampon

| | % w/w |
|---|---|
| Compound | 0.1 g |
| Inwitor 742 | 0.1 g |
| Hard Fat to (Wite psol W35) | 2.0 g |

Example 196 1% Gel

| | % w/w |
|---|---|
| Compound | 1.00 |
| Poloxamer 407 | 25.00 |
| Ethanol | 20.00 |
| Methyl paraben | 0.15 |
| Propyl paraben | 0.05 |
| Purified water to | 100.00 |

Example 197 Pessary

| | g |
|---|---|
| Compound | 0.10 |
| Glycerol | 2.10 |
| Gelatin | 0.42 |
| Purified water to | 3.00 |

Example 198 1% Foam

| | % w/w |
|---|---|
| Compound | 1.00 |
| Polyoxyethylene cetyloleylalcohol | 2.10 |
| Polyoxyethylene oleylalcohol | 0.28 |
| Polyoxyethylene lanolin alcohol | 0.19 |
| 2-methyl-pentane-2,4-diol | 2.15 |
| Dichlorodifluoromethane | 2.00 |
| Dichlorotetrafluoroethane | 5.00 |
| Purified water to | 100.00 |

Example 199 1% Ointment

| | % w/w |
|---|---|
| Compound | 1.00 |
| Plastibase 50 W to | 100.00 |

Example 200 1% Insert

| | g |
|---|---|
| Matrix: | |
| Compound | 0.1 |
| Magnesium sulphate to | 3.0 |

FORMULATION EXAMPLES

Shell:
Ethyl vinyl acetate
with pathway to the exterior and a thread attached.

EXAMPLE 201 IN VITRO ACTIVITY AGAINST *CANDIDA ALBICANS*

Minimum Inhibition Concentrations (MICs) of compounds of the present invention vs. *C. albicans* were determined. The results are shown in table 11.

| Media | Yeast Nitrogen Base (YNB) Broth |
|---|---|
| Difco YNB | 6.7 g |
| D-glucose | 10.0 g |
| L-asparigine | 1.5 g |
| distilled water | 100 $cm^3$ |

The solution was filter sterilised with a 0.45 μm membrane filter unit and was then further diluted with sterile distilled water (SDW)-YNB solution: SDW (1:5).

TABLE 11

Minimum Inhibition Concentrations (MIC) vs. *C. albicans.*

| Compounds of Example Number | Salt | MIC ($\mu g/cm^3$) |
|---|---|---|
| 1 | $HNO_3$ | 1.6 |
| 2 | HBr | 1.6 |
| 3 | H-fumarate | 6.2 |
| 5 | HCl | 6.2 |
| 13 | HCl | 6.2 |
| 22 | HCl | 3.1 |
| 23 | HCl | 6.2 |
| 31 | HCl | 6.2 |
| 45 | HCl | 6.2 |
| 50 | HCl | 6.2 |
| 52 | HCl | 6.2 |
| 57 | HCl | 6.2 |
| 6 | HBr | 25 |
| 39 | $HNO_3$ | 1.6 |
| 107 | HCl | 25 |
| 128 | $HNO_3$ | 25 |
| 144 | HCl | 1.6 |

I claim:
1. A compound of formula (X):

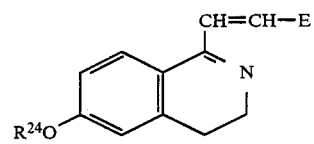

or a salt or acyl derivative thereof,
wherein $R^{24}$ is $C_{3-10}$ alkyl, benzyl, phenyl, $C_{3-7}$ cycloalkyl, $C_{4-8}$ cycloalkylalkyl and $C_{3-10}$ alkenyl each optionally substituted by halogen, cyano, hydroxy, thio, nitro, $C_{1-3}$ alkoxy or $C_{1-3}$ alkylthio wherein the alkoxy and alkylthio groups are optionally further substituted by halogen, hydroxy, thio, $C_{1-2}$ alkoxy or $C_{1-2}$ alkythio, and E represents five or six membered ring having one heteroatomic ring member chosen from oxygen, sulphur and nitrogen, the ring being optionally substituted by one or two groups chosen from hydroxy, $C_{1-2}$ alkoxy, halogen, $C_{1-2}$ alkyl, nitro or cyano.

2. A compound selected from the group consisting of:
(E)-6-Butyloxy-1-(2-cyclohexylvinyl)-3,4-dihydroisoquinoline
6-Benzyloxy-1-[2-cyclohexylvinyl]-3,4-dihydroisoquinoline
6-Butyloxy-3,4-dihydro-1-styrylisoquinoline
1-(2-Chlorostyryl)-3,4-dihydro-6-propyloxyisoquinoline
(E)-1-(2-Cyclohexylvinyl)-3,4-dihydro-6-(2-methylpropyloxy)isoquinoline
(E)-1-(2-Cyclohexylvinyl)-3,4-dihydro-6-propyloxyisoquinoline
(E)-1-(Cyclohexylvinyl)-6-hexyloxy-3,4-dihydroisoquinoline
(E)-6-(4-Chlorobenzyloxy)-1-(2-cyclohexylvinyl)-3,4-dihydroisoquinoline
(E)-6-Benzyloxy-1-[2-(cyclohex-3-enyl)vinyl]-3,4-dihydroisoquinoline
6-Butyloxy-3,4-dihydro-1-(2,5-dimethoxystyryl)isoquinoline
6-Butyloxy-3,4-dihydro-1-(3,4,5-trimethoxystyryl)isoquinoline
6-Butyloxy-1-(2-chlorostyryl)-3,4-dihydroisoquinoline
6-Butyloxy-3,4-dihydro-1-(4-cyanostyryl)isoquinoline
6-Butyloxy-3,4-dihydro-1-(2,4-dimethoxystyryl)isoquinoline
6-Butyloxy-1-(4-t-butylstyryl)-3,4-dihydroisoquinoline
6-Butyloxy-3,4-dihydro-1-(4-isopropylstyryl)isoquinoline
6-Butyloxy-3,4-dihydro-1-(4-methylstyryl)isoquinoline
6-Butyloxy-3,4-dihydro-1-(3,4-dimethoxystyryl)isoquinoline
6-Butyloxy-3,4-dihydro-1-(4-nitrostyryl)isoquinoline
6-Butyloxy-3,4-dihydro-1-(2,4-dimethylstyryl)isoquinoline
6-Butyloxy-1-(2,4-dichlorostyryl)-3,4-dihydroisoquinoline
6-Butyloxy-1-(4-chlorostyryl)-3,4-dihydroisoquinoline
(E)-6-Butyloxy-1-(2-pentafluorophenyl)vinyl-3,4-dihydroisoquinoline
6-Butyloxy-3,4-dihydro-1-(4-phenylstyryl)isoquinoline
6-Butyloxy-1-(2,4-dichlorostyryl)-3,4-dihydro-7-methyl-isoquinoline
3,4-Dihydro-1-(4-methylstyryl)-6-propyloxyisoquinoline
1-(4-Cyanostyryl)-3,4-dihydro-6-propyloxyisoquinoline
3,4-Dihydro-6-propyloxy-1-styrylisoquinoline
3,4-Dihydro-1-(2,5-dimethoxystyryl)-6-propyloxyisoquinoline
1-(4-Chlorostyryl)-3,4-dihydro-6-propyloxyisoquinoline
1-(2,4-Dichlorostyryl)-3,4-dihydro-6-propyloxyisoquinoline
3,4-Dihydro-1-(4-phenylstyryl)-6-propyloxyisoquinoline
1-(2,4-Dichlorostyryl)-3,4-dihydro-6-(3,3-dimethylbutyloxy)isoquinoline
1-(2-Chlorostyryl)-3,4-dihydro-6-(3,3-dimethylbutyloxy)isoquinoline
1-(4-Chlorostyryl)-3,4-dihydro-6-(3,3-dimethylbutyloxy)isoquinoline
6-Cyclohexylmethoxy-3,4-dihydro-1-styrylisoquinoline
1-(4-Cyanostyryl)-6-cyclohexylmethoxy-3,4-dihydroisoquinoline
1-(4-Chlorostyryl)-6-cyclohexylmethoxy-3,4-dihydroisoquinoline
1-(2-Chlorostyryl)-6-cyclohexylmethoxy-3,4-dihydroisoquinoline
1-(2,4-Dichlorostyryl)-6-cyclohexylmethoxy-3,4-dihydroisoquinoline
(E)-6-Cyclohexylmethoxy-1-(2-(pentafluorophenyl)vinyl)-3,4-dihydroisoquinoline
1-(4-Chlorostyryl)-3,4-dihydro-6-(2-methylpropyloxy)-3-methylisoquinoline
1-(2,4-Dichlorostyryl)-3,4-dihydro-3-methyl-6-(2-methylpropyloxy)isoquinoline
1-(2-Chlorostyryl)-3,4-dihydro-3-methyl-6-(2-methylpropyloxy)isoquinoline
6-(But-3-enyloxy)-1-(4-chlorostyryl)-3,4-dihydroisoquinoline
6-(But-3-enyloxy)-1-(2,4-dichlorostyryl)-3,4-dihydroisoquinoline
1-(2-Chlorostyryl)-3,4-dihydro-6-(2-methylpropyloxy)isoquinoline
1-(2,4-Dichlorostyryl-3,4-dihydro-6-(2-methylpropyloxy)-isoquinoline
1-(2,4-Dichlorostyryl)-3,4-dihydro-6-(3-methylbutyloxy)isoquinoline
1-(4-Chlorostyryl)-3,4-dihydro-6-(3-methylbutyloxy)isoquinoline
1-(4-Chlorostyryl)-3,4-dihydro-6-(2-methylpropyloxy)isoquinoline
6-Benzyloxy-1-(4-cyanostyryl)-3,4-dihydroisoquinoline
6-Benzyloxy-3,4-dihydro-1-styrylisoquinoline
6-Benzyloxy-1-(2-chlorostyryl)-3,4-dihydroisoquinoline
6-Benzyloxy-3,4-dihydro-1-(2,5-dimethoxystyryl)isoquinoline
6-Benzyloxy-3,4-dihydro-1-(2,4-dimethoxystyryl)isoquinoline
6-Benzyloxy-1-(4-chlorostyryl)-3,4-dihydroisoquinoline
6-Benzyloxy-3,4-dihydro-1-(4-methylstyryl)isoquinoline
6-Benzyloxy-3,4-dihydro-1-(4-isopropylstyryl)isoquinoline
6-Benzyloxy-1-(4-t-butylstyryl)-3,4-dihydroisoquinoline
6-Benzyloxy-3,4-dihydro-1-(2,4-dimethylstyryl)isoquinoline
6-Benzyloxy-3,4-dihydro-1-(4-nitrostyryl)isoquinoline
6-Benzyloxy-1-(2,4-dichlorostyryl)-3,4-dihydroisoquinoline
(E)-6-Benzyloxy-1-(2-(pentafluorophenyl)vinyl)-3,4-dihydroisoquinoline
1-(4-Chlorostyryl)-3,4-dihydro-6-phenoxy-isoquinoline
1-(2,4-Dichlorostyryl)-3,4-dihydro-6-phenoxyisoquinoline
6-(4-Chlorophenoxy)-1-(4-chlorostyryl)-3,4-dihydroisoquinoline
6-(4-Chlorophenoxy)-3,4-dihydro-1-(4-nitrostyryl)isoquinoline
6-(4-Chlorophenoxy)-1-(2,4-dichlorostyryl)-3,4-dihydroisoquinoline
6-(4-Chlorophenoxy)-3,4-dihydro-1-styrylisoquinoline
6-(4-t-Butylphenoxy)-1-(2,4-dichlorostyryl)-3,4-dihydroisoquinoline
6-(4-t-Butylphenoxy)-1-(4-chlorostyryl)-3,4-dihydroisoquinoline
6-(4-t-Butylphenoxy)-3,4-dihydro-1-styrylisoquinoline
6-Hexyloxy-3,4-dihydro-1-styrylisoquinoline
1-(4-Cyanostyryl)-6-hexyloxy-3,4-dihydroisoquinoline
1-(2-Chlorostyryl)-3,4-dihydro-6-hexyloxyisoquinoline
1-(4-Chlorostyryl)-6-hexyloxy-3,4-dihydroisoquinoline 1-(2,4-Dichlorostyryl)-6-hexyloxy-3,4-dihydroisoquinoline
6-(4-t-Butylbenzyloxy)-1-(4-cyanostyryl)-3,4-dihydroisoquinoline
6-(4-t-Butylbenzyloxy)-3,4-dihydro-1-styrylisoquinoline
6-(4-t-Butylbenzyloxy)-1-(2,4-dichlorostyryl)-3,4-dihydroisoquinoline
6-Benzyloxy)-1-(4-phenylstyryl)-3,4-dihydroisoquinoline
6-(4-Chlorobenzyloxy)-3,4-dihydro-1-styrylisoquinoline
6-(4-Chlorobenzyloxy)-1-(4-chlorostyryl)-3,4-dihydroisoquinoline
6-(4-Chlorobenzyloxy)-1-(2,4-dichlorostyryl)-3,4-dihydroisoquinoline
6-(2-Chlorobenzyloxy)-1-(4-cyanostyryl)-3,4-dihydroisoquinoline
6-(2-Chlorobenzyloxy)-1-(2-chlorostyryl)-3,4-dihydroisoquinoline
6-(2-Chlorobenzyloxy)-1-(2,4-dichlorostyryl)-3,4-dihydroisoquinoline
6-(2,4-Dichlorobenzyloxy)-1-(4-cyanostyryl)-3,4-dihydroisoquinoline
1-(4-Chlorostyryl)-6-(2,4-dichlorobenzyloxy)-3,4-dihydroisoquinoline
6-(2,4-Dichlorobenzyloxy)-3,4-dihydro-1-styrylisoquinoline
6-(2,4-Dichlorobenzyloxy)-1-(2,4-dichlorostyryl)-3,4-dihydroisoquinoline
6-Benzyloxy-3,4-dihydro-1-(3,4,5-trimethoxystyryl)isoquinoline
3,4-Dihydro-3-methyl-6-iso-propyloxy-1-styrylisoquinoline,
3,4-Dihydro-6-ethoxy-3-propyl-1-styrylisoquinoline,
3,4-Dihydro-3-ethyl-6-propyloxy-1-styrylisoquinoline,
1-(2-Chlorostyryl)-6-(3-trifluoromethyl benzyloxy)-3,4-dihydroisoquinoline
1-(4-Cyanostyryl)-6-(3-trifluoromethyl benzyloxy)-3,4-dihydroisoquinoline
3,4-Dihydro-1-styryl-6-(3-trifluoromethyl benzyloxy)isoquinoline
6-Butyloxy-1-(2-fluorostyryl)-3,4-dihydroisoquinoline
6-Benzyloxy-1-(2-fluorostyryl)-3,4-dihydroisoquinoline
(E)-6-Butyloxy-3,4-dihydro-1-[2-(4-bromo-2-thienyl)vinyl]isoquinoline
(E)-6-Butyloxy-3,4-dihydro-1-[2-(5-bromo-2-thienyl)vinyl]isoquinoline
(E)-6-Benzyloxy-3,4-dihydro-1-[2-(2-thienyl)vinyl isoquinoline
(E)-6-Butyloxy-3,4-dihydro-1-[2-(2-thienyl)vinyl isoquinoline
(E)-6-Benzyloxy-3,4-dihydro-1-(3-thienyl)vinyl isoquinoline
(E)-6-Butyloxy-3,4-dihydro-1-(3-thienyl)vinylisoquinoline
(E)-6-Benzyloxy-3,4-dihydro-1-[2-(4-bromo-2-thienyl)vinyl]isoquinoline
(E)-6-Benzyloxy-3,4-dihydro-1-[2-(5-bromo-2-thienyl)vinyl] isoquinoline
(E)-6-Butyloxy-1-[2-(2-furyl)vinyl]-3,4-dihydroisoquinoline
(E)-6-Benzyloxy-1-[2-(2-furyl)vinyl]-3,4-dihydroisoquinoline
(E)-6-(4-Chlorobenzyloxy)-1-[2-(2-furyl)vinyl]-3,4-dihydroisoquinoline
(E)-3,4-Dihydro-6-propyloxy-1-[2-(5-nitro-2-furyl)]vinyl isoquinoline
(E)-6-Butyloxy-3,4-dihydro-1-[2-(5-nitro-2-furyl)]vinyl isoquinoline
(E)-6-Benzyloxy-3,4-dihydro-1-[2-(5-nitro-2-furyl)]vinyl isoquinoline
(E)-6-Butyloxy-3,4-dihydro-1-[2-(3-methyl-2-thienyl)vinyl]isoquinoline
(E)-3,4-Dihydro-1-[2-(3-methyl-2-thienyl)vinyl]-6-propyloxyisoquinoline
(E)-6-Benzyloxy-3,4-dihydro-1-[2-(3-methyl-2-thienyl)vinyl]isoquinoline
(E)-3,4-Dihydro-1-[2-(5-methyl-2-furyl)vinyl]-6-propyloxy-isoquinoline
(E)-6-Butyloxy-3,4-dihydro-1-[2-(5-methyl-2-furyl)vinyl]isoquinoline
(E)-6-Benzyloxy-3,4-dihydro-1-[2-(5-methyl-2-furyl)vinyl]isoquinoline
(E)-3,4-Dihydro-1-[2-(5-nitro-2-thienyl)vinyl]-6-propyloxyisoquinoline
(E)-6-Butyloxy-3,4-dihydro-1-[2-(5-nitro-2-thienyl)vinyl]isoquinoline
(E)-6-Butyloxy-3,4-dihydro-1-[2-(4-pyridyl)-vinyl]isoquinoline
(E)-6-Benzyloxy-3,4-dihydro-1-[2-(4-pyridyl)-vinyl]isoquinoline
(E,E)-6-Benzyloxy-3,4-dihydro-1-(4-phenylbuta-1,3-dienyl)isoquinoline
(E,E)-3,4-Dihydro-1-(penta-,1,3-dienyl)-6-propyloxyisoquinoline
(E,E)-6-Butyloxy-3,4-dihydro-1-(penta-1,3-dienyl)isoquinoline
(E,E)-6-Hexyloxy-3,4-dihydro-1-(penta-1,3-dienyl)isoquinoline
(E,E)-6-Benzyloxy-3,4-dihydro-1-(penta-1,3-dienyl)isoquinoline
(E)-3,4-Dihydro-1-[2-(2-naphthyl)vinyl]-6-propyloxyisoquinoline
(E)-6-Butyloxy-3,4-dihydro-1-[2-(2-naphthyl)-vinyl]isoquinoline
(E)-6-Benzyloxy-3,4-dihydro-1-[2-(2-naphthyl)-vinyl]isoquinoline
(E)-3,4-Dihydro-1-[2-(1-naphthyl)vinyl]-6-propyloxyisoquinoline
(E)-6-Butyloxy-3,4-dihydro-1-[2-(1-naphthyl)vinyl]isoquinoline
(E)-6-Benzyloxy-3,4-dihydro-1-[2-(1-naphthyl)vinyl]isoquinoline
3,4-Dihydro-1-prop-1-enyl-6-propyloxyisoquinoline
6-Benzyloxy-3,4-dihydro-1-prop-1-enylisoquinoline
(E)-6-Butyloxy-3,4-dihydro-1-(penta-1,3-dienyl)isoquinoline
6-Butyloxy-3,4-dihydro-1-(4-phenylbuta-1,3-dienyl)isoquinoline
1-(2-(9-Anthryl)vinyl)-6-benzyloxy-3,4-dihydroisoquinoline,
1-(2-(9-Anthryl)vinyl)-3,4-dihydro-6-propyloxy isoquinoline,
3,4-Dihydro-1-(2-(9-phenanthryl)vinyl)-6-propyloxyisoquinoline,
6-Butyloxy-3,4-dihydro-1-(2-(5-methyl-2-thienyl)vinyl)isoquinoline,
3,4-Dihydro-1-(2-(5-methyl-2-thienyl)vinyl)-6-propyloxyisoquinoline,
6-Benzyloxy-3,4-dihydro-1-(2-(5-methyl-2-thienyl)vinyl)isoquinoline,
(Z)-6-Butyloxy-1-(1-bromo-2-phenylvinyl)-3,4-dihydroisoquinoline
(Z)-6-Benzyloxy-1-(1-bromo-2-phenylvinyl)-3,4-dihydroisoquinoline (Z)-6-Butyloxy-1-(1-fluoro-2-phenylvinyl)-3,4-dihydroisoquinoline
(Z)-6-Butyloxy-1-(1-chloro-2-phenylvinyl-3,4-dihydroisoquinoline
(Z)-6-Benzyloxy-1-(1-chloro-2-phenylvinyl)-3,4-dihydroisoquinoline
(E)-6-Benzyloxy-3,4-dihydro-1-(2-phenyl)-1-methylvinyl)isoquinoline
(E)-6-Butyloxy-3,4-dihydro-1-(2-phenyl-1-methylvinyl)isoquinoline
(Z)-6-Benzyloxy-1-(1-fluoro-2-phenylvinyl)-3,4-dihydroisoquinoline
1-(2,4-Dichlorostyryl)-3,4-dihydro-6,7-dipropyloxyisoquinoline
1-(4-Chlorostyryl)-3,4-dihydro-3-methyl-6,7-dipropyloxy isoquinoline
6,7-Dibutyloxy-1-(4-chlorostyryl)-3,4-dihydroisoquinoline
1-(2,4-Dichlorostyryl)-3,4-dihydro-3-methyl-6,7-dipropyloxyisoquinoline
6,7-Dibutyloxy-1-(4-chlorostyryl)-3-methyl-isoquinoline
6-Butyloxy-1-(2,4-dichlorostyryl)-7-ethoxy-3,4-dihydroisoquinoline
7-Butyloxy-1-(2,4-dichlorostyryl)-6-ethoxy-3,4-dihydroisoquinoline
7-Butyloxy-1-(4-chlorostyryl)-6-ethoxy-3,4-dihydroisoquinoline
6-Butyloxy-1-(4-chlorostyryl)-7-ethoxy-3,4-dihydroisoquinoline
1-(4-Chlorostyryl)-3,4-dihydro-6,7-dipentyloxyisoquinoline
1-(4-Chlorostyryl)-6,7-dihexyloxy-3,4-dihydroisoquinoline
3,4-Dihydro-1-(4-hydroxystyryl)-6,7-dipropyloxyisoquinoline
3,4-Dihydro-1-(4-trifluoromethylstyryl)-6,7-dipropyloxyisoquinoline
1-(4-Chlorostyryl)-3,4-dihydro-6,7-dipropyloxy isoquinoline
6,7-Bisbenzyloxy-1-(2-Chlorostyryl)-3,4-dihydroisoquinoline
6,7-Bisbenzyloxy-1-(2,4-dichlorostyryl)-3,4-dihydroisoquinoline
5,6-Bis(benzyloxy)-3,4-dihydro-1-styrylisoquinoline
5,6-Bis(benzyloxy)-1-(4-chlorostyryl)-3,4-dihydroisoquinoline
5,6-Bis(benzyloxy)-1-(2,4-dichlorostyryl)-3,4-dihydroisoquinoline
5-Benzyloxy-3,4-dihydro-8-methoxy-1-styryl-isoquinoline
5-Benzyloxy-1-(4-cyanostyryl)-3,4-dihydro-8-methoxyisoquinoline
6-Benzyloxy-1-(4-chlorostyryl)-3,4-dihydro-7-methoxy-5-propylisoquinoline
6-Benzyloxy-1-(2-chlorostyryl)-3,4-dihydro-7-methoxy-5-propylisoquinoline
6-Hydroxy-3,4-dihydro-7-methoxy-5-propyl-1-styrylisoquinoline
1-(2,4-Dichlorostyryl)-3,4-dihydro-6-hydroxy-7-methoxy-5-propylisoquinoline
1-(2-Chlorostyryl)-3,4-dihydro-6-hydroxy-7-methoxy-5-propylisoquinoline
1-(4-Chlorostyryl)-3,4-dihydro-5-hydroxy-8-methoxyisoquinoline
6-Butyloxy-1-(2,4-dichlorostyryl)-3,4-dihydro-7-methylisoquinoline
1-(4-Acetoxystyryl)-3,4-dihydro-6,7-dipropyloxy isoquinoline
1,2,3,4-Tetrahydro-6,7-dibutyloxy-1-(4-chlorostyryl)isoquinoline
1-(4-Chlorostyryl)-1,2,3,4-tetrahydro-6,7-dipropyloxy isoquinoline
3,4-Dihydro-3,3-dimethyl-6-propyloxy-1-styrylisoquinoline,
3,4-Dihydro-3,3,4,4-tetramethyl-6-propyloxy-1-styrylisoquinoline,
6-Butyloxy-3,4-dihydro-3,3-dimethyl-1-styrylisoquinoline,
3,4-Dihydro-3,3-dimethyl-6-heptyloxy-1-styrylisoquinoline,
3,4-Dihydro-4,4-dimethyl-6-propyloxy-1-styrylisoquinoline,
4-Butyloxystyryl-3,4-dihydroisoquinoline,
or a salt or acyl derivative thereof.

3. (E)-1-(2-Cyclohexylvinyl)-3,4-dihydro-6-propyloxy isoquinoline or a salt thereof.

4. A phosphoric acid salt of the compound of claim 3.

5. A method of treatment of a protozoal infection in man or animals which method comprises the administration of an effective nontoxic antiprotozoal amount of a compound according to claim 1 or 2 or pharmaceutically acceptable salt thereof.

* * * * *